United States Patent
Sætrom

(10) Patent No.: US 10,704,044 B2
(45) Date of Patent: *Jul. 7, 2020

(54) ALBUMIN PRODUCTION AND CELL PROLIFERATION

(71) Applicant: MiNA THERAPEUTICS LIMITED, London (GB)

(72) Inventor: Pål Sætrom, Trondheim (NO)

(73) Assignee: MiNA THERAPEUTICS LIMITED, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/915,275

(22) Filed: Mar. 8, 2018

(65) Prior Publication Data
US 2018/0201932 A1 Jul. 19, 2018

Related U.S. Application Data

(60) Continuation of application No. 15/656,000, filed on Jul. 21, 2017, now Pat. No. 9,944,930, which is a division of application No. 15/013,866, filed on Feb. 2, 2016, now Pat. No. 9,745,579, which is a division of application No. 14/128,147, filed as application No. PCT/GB2012/051422 on Jun. 20, 2012, now Pat. No. 9,284,553.

(60) Provisional application No. 61/499,637, filed on Jun. 21, 2011.

(51) Int. Cl.
| | |
|---|---|
| C12N 15/113 | (2010.01) |
| A61K 31/713 | (2006.01) |
| A61K 31/7105 | (2006.01) |
| A61P 35/00 | (2006.01) |
| A61P 1/16 | (2006.01) |
| C12N 15/11 | (2006.01) |

(52) U.S. Cl.
CPC .......... *C12N 15/113* (2013.01); *A61K 31/713* (2013.01); *A61K 31/7105* (2013.01); *A61P 1/16* (2018.01); *A61P 35/00* (2018.01); *C12N 15/111* (2013.01); *C12N 2310/113* (2013.01); *C12N 2320/30* (2013.01); *Y02A 90/26* (2018.01)

(58) Field of Classification Search
None
See application file for complete search history.

(56) References Cited

U.S. PATENT DOCUMENTS

| 6,306,655 B1 | 10/2001 | Monia et al. |
| 2011/0077206 A1 | 3/2011 | Xie et al. |

FOREIGN PATENT DOCUMENTS

| JP | 2008-538896 | 11/2008 |
| JP | 2008-538896 A | 11/2008 |
| WO | 04/045543 | 6/2004 |
| WO | 2004045543 A2 | 6/2004 |
| WO | 06/113246 | 10/2006 |
| WO | 2006/113246 A2 | 10/2006 |
| WO | 2006113246 | 10/2006 |
| WO | 2006113246 A2 | 10/2006 |
| WO | 10/151755 | 12/2010 |
| WO | 2010151755 A2 | 12/2010 |

OTHER PUBLICATIONS

Dhawan, P. et al. CCAAT Enhancer-Binding Protein is a molecular target of 1,25-Dihydroxyvitamin 03 in MCF-7 breast cancer cells. J. Biol. Chem. 2008.284(5):3086-3095.
Chen, Y. et al. Transplantation pf human hepaticytes cultured and deleted variant of hepatocyte growth factor prolongs the survival of mice with acute liver failure. Transplanation. 2005. 79(10):1378-1385.
Ishiyama, T. et al. Expression of HNFs and C/EBP alpha is correlated with immunocytochemical differentiation of cell lines derived from human hepatocellular carcinomas, hepatoblastomas and immortalized hepatocytes. Cancer Science. 2003. 94(9):757-763.
Kratz, F. Albumin, a versatile carrier in oncology. Int'l J. Clin. Pharm. Ther. 2010. 48(7):453-455.
Madhorta, R. et al. Recent developments in the treatment of alcohol hepatitis. Monthly J. Assoc. Physicians. 2003. 96(6):391-400.
McCormick, P.A. et al., Intravenous albumin infusion is an effective therapy for hyponatraemia in cirrhotic patients with ascites. Gut. 31(2):204-207.
International Search Report and Written Opinion for PCT/GB2012/051422, dated Sep. 26, 2012.
Gery, Sigal et al. "Clin Cancer Res", 2005, vol. 11, No. 9, May 1, 2005, p. 3184-3190.
Wang, Guo-Li et al. "Exp Cell Res", Apr. 15, 2008, vol. 314, No. 7, p. 1626-1639.
Office Action dated Mar. 9, 2016 received in corresponding Japanese application No. 2014-516440.
Lu, G.-D. et al., "C/EBP α Is Up-regulated in a Subset of Hepatocellular Carcinomas and Plays a Role in Cell Growth and Proliferation" (2010) Gastroenterology 139:632-643.
Communication pursuant to Article 94(3) EPC dated Nov. 28, 2016 received in corresponding European application No. 12 730 246.1.
Ishiyama, T. et al., "Expression of HNFs and C/EBP alpha is correlated with immunocytochemical differentiation of cell lines derived from human hepatocellular carcinomas, hepatoblastomas and immortalized hepatocytes" (2003) Cancer science 94(9):757-763.

(Continued)

*Primary Examiner* — Sean McGarry
(74) *Attorney, Agent, or Firm* — DT Ward, PC; Donna T. Ward; Heng Zhu

(57) ABSTRACT

The present invention provides short activating RNA molecules which up-regulate albumin production. The present invention also provides methods of up-regulating albumin production, such methods involving the use of short activating RNA molecules capable of increasing the expression of albumin. The present invention also provides the use of the short activating RNA molecules in therapy, such as treating or preventing a hyperproliferative disorder and/or a disorder characterised by hypoalbuminemia.

13 Claims, 16 Drawing Sheets

Specification includes a Sequence Listing.

(56) References Cited

OTHER PUBLICATIONS

Yong, C. et al., "Transplantation of human hepatocytes cultured with deleted variant of hepatocyte growth factor prolongs the survival of mice with acute liver failure" (2005) Transplantation 79(10):1378-1385.

Madhotra R. et al., "Recent developments in the treatment of alcoholic hepatitis" (2003) Q J Med 96(3):91-400.

McCormick P.A. et al., "Intravenous albumin infusion is an effective therapy for hyponatraemia in cirrhotic patients with ascites" (1990) GUT 31(2):204-207.

Dhawan P. et al., "CCAAT Enhancer-Binding Protein is a molecular target of 1,25-Dihydroxyvitamin 03 in MCF-7 breast cancer cells" (2008) J of Biological Chem 284(5):3086-3095.

Examination Report dated Jun. 19, 2019 in corresponding Indian application No. 298/DELNP/2014 entitled, "Albumin Production and Cell Proliferation".

Office Action dated May 17, 2018, in co-pending Japanese application No. 2016-160357 entitled, "Albumin Production and Cell Proliferation".

Office Action dated Jul. 17, 2018, in co-pending Korean application No. 10-2014-7001446 entitled, "Albumin Production and Cell Proliferation".

Extended European Search Report dated Dec. 21, 2018 received in corresponding European Patent Application No. 18189270.4.

Tadashi Ishiyama et al.: "Expression of HNFs and C/EBP alpha is correlated with immunocytochemical differentiation of cell lines derived from human hepatocellular carcinomas, hepatobliastomas and immortalized hepatocytes", Cancer Science, vol. 94, No. 9, Sep. 1, 2003 (Sep. 1, 2003), pp. 757-763.

Chen Yong et al.: "Transplantation of human hepatocytes cultured with deleted variant of hepatocytes growth factor prolongs the survivial of mice with acute liver failure", Transplantation (Hagerstown), vol. 79, No. 10, May 2005 (May 2005), pp. 1378-1385.

Madhotra R. et al.: "Recent developments in the treatment of alcoholic hepatitis", QJM: Monthly Journal of the Association of Physicians, vol. 96, No. 6, Jun. 2003 (Jun. 2003), pp. 391-400.

McCormick P.A. et al.: "Intravenous albumin infusion is an effective therapy for hyponatraemia in cirrhotic patients wit ascites", GUT, vol. 31, No. 2, Feb. 1990 (Feb. 1990), pp. 204-207.

Kratz, F.: "Albumin, a versitile carrier in oncology", International Journal of Clinical Pharmacology and Therapeutics, Dustri-Verlag, Deisenhofen-Muenchen, DE, vol. 48, No. 7, Jul. 1, 2010 (Jul. 1, 2010), pp. 453-455.

Preliminary Rejection dated Jan. 25, 2019 received in corresponding Japanese application No. 10-2014-7001446.

Li, L.-C. et al., "Small dsRNAs induce transcriptional activation in human cells" (2006) PNAS 103(46):17337-17342.

Huang, V. et al., "RNAa Is Conserved in Mammalian Cells" (2010) PLoS ONE 5(1):e8848.

Notice of Reasons for Rejection dated Jan. 29, 2020 in corresponding Japanese application No. 2019-024365, entitled "Albumin Production and Cell Proliferation".

Notice of Preliminary Rejection dated Feb. 14, 2020 in corresponding Korean application No. 1020197031287, entitled "Albumin Production and Cell Proliferation".

Fig. 1
Mechanism A 110
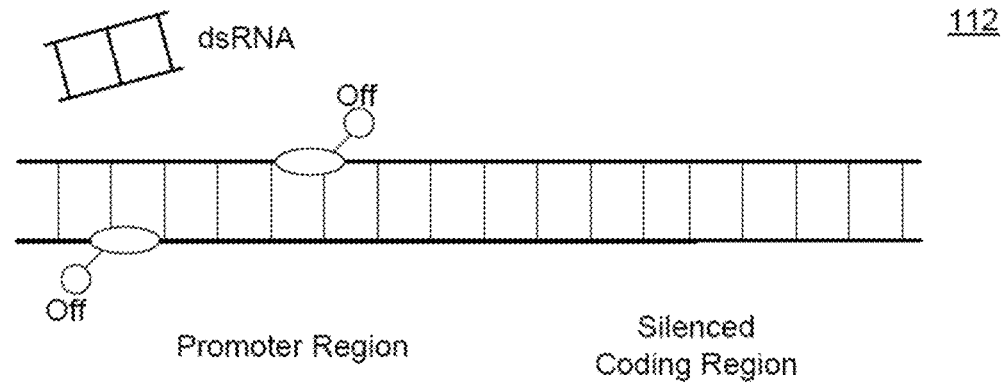
Mechanism B 120
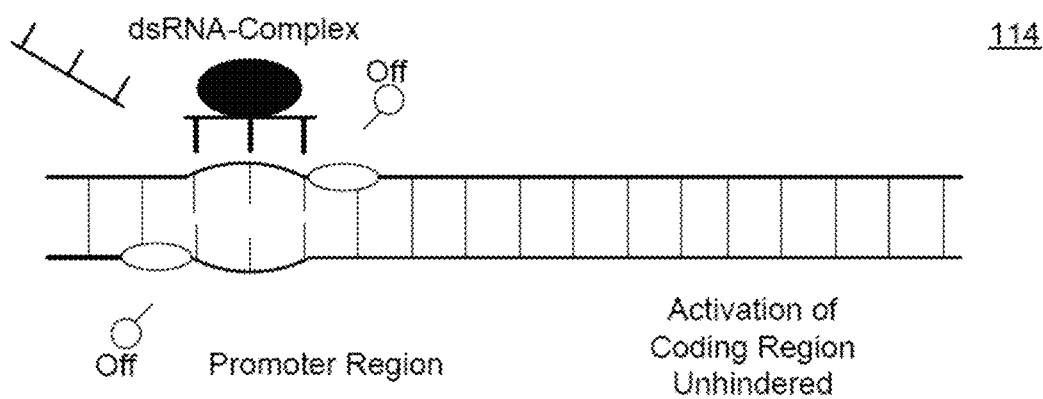
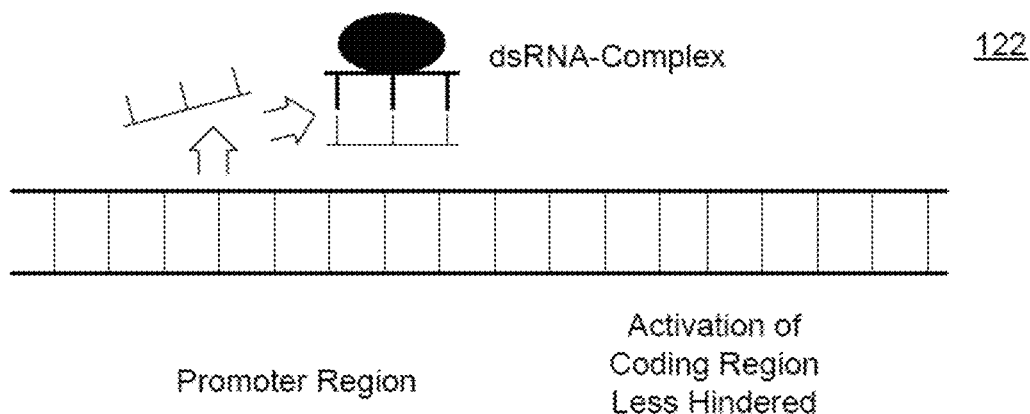

Relative expression of Albumin (%) n=2

| Condition | % Albumin expression |
|---|---|
| Scrmbl RNA | 100 |
| Alb-PR1 saRNA | 132 (±3.3) |
| Alb-PR2 saRNA | 134 (±4.2) |
| Alb-PR3 saRNA | 158 (±5.7) |
| Alb-PR4 saRNA | 144 (±4.5) |

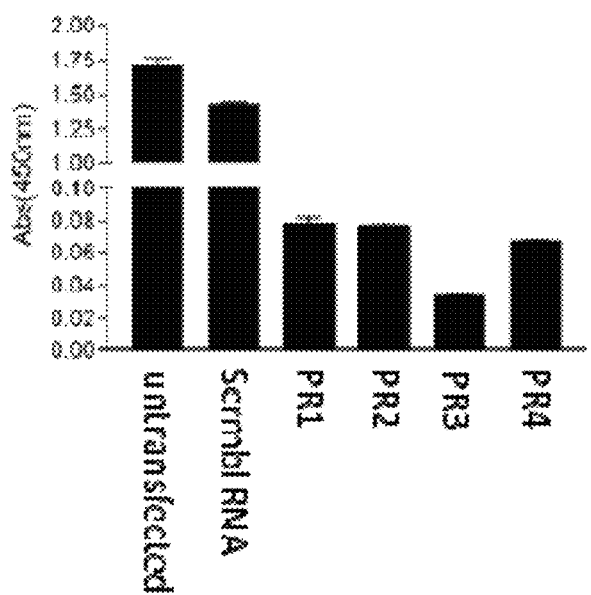

Fig. 6
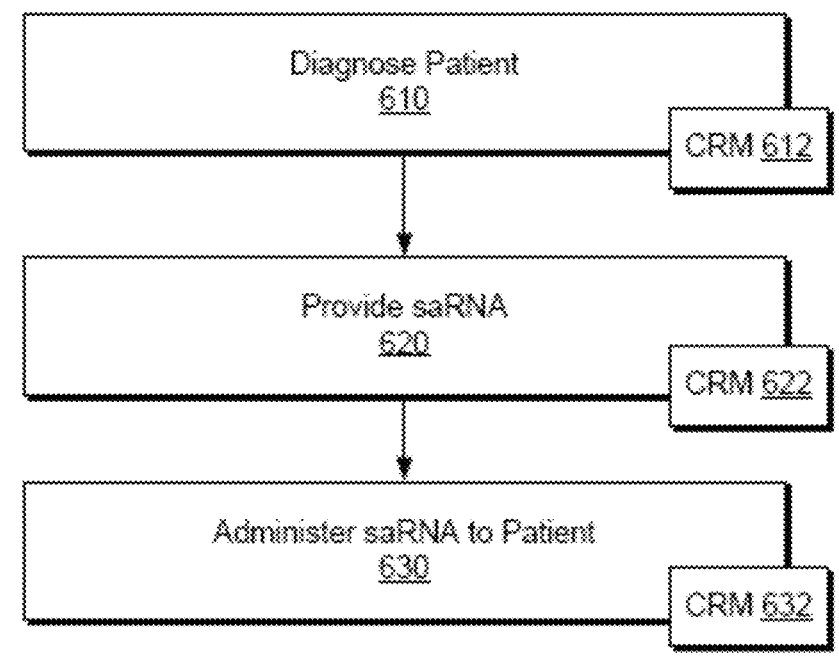
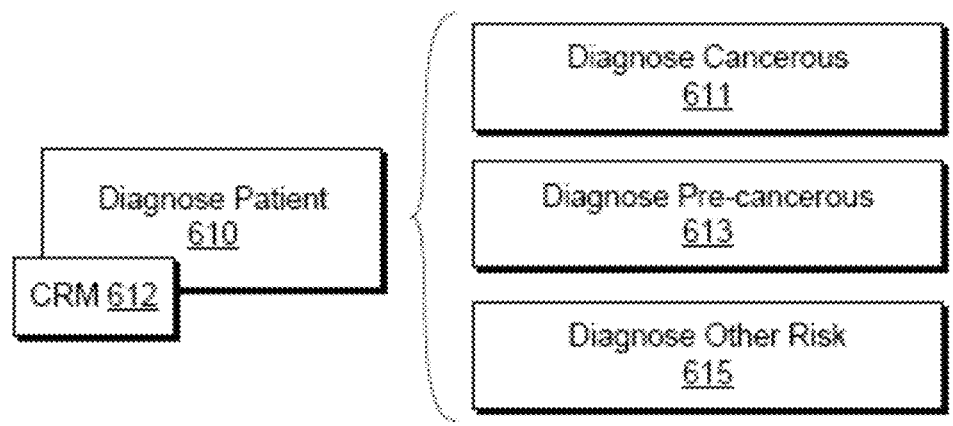

SEQUENCE LISTING

```
<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tccagcactg cctgcggtga                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tccgtcacgc actgggagga                                                     20

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gagaaaatct ggcaccacac c                                                   21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4 ataccctcg tagatgggca c                                                    21
```

```
<210> SEQ ID NO 5
<211> LENGTH: 19
<212> TYPE: RNA
<213> ORGANISM: Homo sapiens

<400> SEQUENCE: 5
ccuuguaaga cuucacaaa                                                19

<210> SEQ ID NO 6
<211> LENGTH: 19
<212> TYPE: RNA
<213> ORGANISM: Homo sapiens

<400> SEQUENCE: 6
uuugugaagu cuuacaagg                                                19

<210> SEQ ID NO 7
<211> LENGTH: 19
<212> TYPE: RNA
<213> ORGANISM: Homo sapiens

<400> SEQUENCE: 7
uggauagguc uuugggaua                                                19

<210> SEQ ID NO 8
<211> LENGTH: 19
<212> TYPE: RNA
<213> ORGANISM: Homo sapiens

<400> SEQUENCE: 8
uaucccaaag accuaucca                                                19

<210> SEQ ID NO 9
<211> LENGTH: 19
<212> TYPE: RNA
<213> ORGANISM: Homo sapiens

<400> SEQUENCE: 9
aagaguuaag ucccaaauu                                                19

<210> SEQ ID NO 10
<211> LENGTH: 19
<212> TYPE: RNA
<213> ORGANISM: Homo sapiens

<400> SEQUENCE: 10
aauuugggac uuaacucuu                                                19

<210> SEQ ID NO 11
<211> LENGTH: 19
<212> TYPE: RNA
<213> ORGANISM: Homo sapiens

<400> SEQUENCE: 11
gacuaaaucc cuuguguau                                                19

<210> SEQ ID NO 12
<211> LENGTH: 19
<212> TYPE: RNA
<213> ORGANISM: Homo sapiens

<400> SEQUENCE: 12
auacacaagg gauuuaguc                                                19
```

<210> SEQ ID NO 13
<211> LENGTH: 19
<212> TYPE: RNA
<213> ORGANISM: Homo sapiens

<400> SEQUENCE: 13
cggucauugu cacugguca                                                19

<210> SEQ ID NO 14
<211> LENGTH: 19
<212> TYPE: RNA
<213> ORGANISM: Homo sapiens

<400> SEQUENCE: 14
ugaccaguga caaugaccg                                                19

<210> SEQ ID NO 15
<211> LENGTH: 19
<212> TYPE: RNA
<213> ORGANISM: Homo sapiens

<400> SEQUENCE: 15
agcugaaagg auucauccu                                                19

<210> SEQ ID NO 16
<211> LENGTH: 19
<212> TYPE: RNA
<213> ORGANISM: Homo sapiens

<400> SEQUENCE: 16
aggaugaauc cuuccagcu                                                19

<210> SEQ ID NO 17
<211> LENGTH: 19
<212> TYPE: RNA
<213> ORGANISM: Homo sapiens

<400> SEQUENCE: 17
acauagcccc agugauuaa                                                19

<210> SEQ ID NO 18
<211> LENGTH: 19
<212> TYPE: RNA
<213> ORGANISM: Homo sapiens

<400> SEQUENCE: 18
uuaaucacug ggacuaugu                                                19

<210> SEQ ID NO 19
<211> LENGTH: 19
<212> TYPE: RNA
<213> ORGANISM: Homo sapiens

<400> SEQUENCE: 19
gaauaagacu uuguccaau                                                19

<210> SEQ ID NO 20
<211> LENGTH: 19
<212> TYPE: RNA
<213> ORGANISM: Homo sapiens

<400> SEQUENCE: 20
auuggacaaa gucuuauuc                                                  19

<210> SEQ ID NO 21
<211> LENGTH: 19
<212> TYPE: RNA
<213> ORGANISM: Homo sapiens

<400> SEQUENCE: 21
gcgcggauuc ucuuucaaa                                                  19

<210> SEQ ID NO 22
<211> LENGTH: 19
<212> TYPE: RNA
<213> ORGANISM: Homo sapiens

<400> SEQUENCE: 22
uuugaaagag aauccgcgc                                                  19

<210> SEQ ID NO 23
<211> LENGTH: 19
<212> TYPE: RNA
<213> ORGANISM: Homo sapiens

<400> SEQUENCE: 23
ccaggaacuc gucguugaa                                                  19

<210> SEQ ID NO 24
<211> LENGTH: 19
<212> TYPE: RNA
<213> ORGANISM: Homo sapiens

<400> SEQUENCE: 24
uucaacgacg aguccugg                                                   19

<210> SEQ ID NO 25
<211> LENGTH: 19
<212> TYPE: RNA
<213> ORGANISM: Homo sapiens

<400> SEQUENCE: 25
gagcuuuggg cccguaaga                                                  19

<210> SEQ ID NO 26
<211> LENGTH: 19
<212> TYPE: RNA
<213> ORGANISM: Homo sapiens

<400> SEQUENCE: 26
ucuuacgggc ccaaagcuc                                                  19

<210> SEQ ID NO 27
<211> LENGTH: 19
<212> TYPE: RNA
<213> ORGANISM: Homo sapiens

<400> SEQUENCE: 27
gguggauacg uuaaagagu                                                  19

<210> SEQ ID NO 28
<211> LENGTH: 19
<212> TYPE: RNA
<213> ORGANISM: Homo sapiens

<400> SEQUENCE: 28
acucuuuaac guauccacc                                                19

<210> SEQ ID NO 29
<211> LENGTH: 19
<212> TYPE: RNA
<213> ORGANISM: Homo sapiens

<400> SEQUENCE: 29
cccagaaugc cugugauca                                                19

<210> SEQ ID NO 30
<211> LENGTH: 19
<212> TYPE: RNA
<213> ORGANISM: Homo sapiens

<400> SEQUENCE: 30
ugaucacagg cauucuggg                                                19

<210> SEQ ID NO 31
<211> LENGTH: 19
<212> TYPE: RNA
<213> ORGANISM: Homo sapiens

<400> SEQUENCE: 31
ccgauguuca guuaucaau                                                19

<210> SEQ ID NO 32
<211> LENGTH: 19
<212> TYPE: RNA
<213> ORGANISM: Homo sapiens

<400> SEQUENCE: 32
auugauaacu gaacaucgg                                                19

<210> SEQ ID NO 33
<211> LENGTH: 19
<212> TYPE: RNA
<213> ORGANISM: Homo sapiens

<400> SEQUENCE: 33
gaagauugcu cgugcaaau                                                19

<210> SEQ ID NO 34
<211> LENGTH: 19
<212> TYPE: RNA
<213> ORGANISM: Homo sapiens

<400> SEQUENCE: 34
auuugcacga gcaaucuuc                                                19

<210> SEQ ID NO 35
<211> LENGTH: 19
<212> TYPE: RNA
<213> ORGANISM: Homo sapiens

<400> SEQUENCE: 35
cagauaugcu ccagugaug                                                19

<210> SEQ ID NO 36
<211> LENGTH: 19
<212> TYPE: RNA
<213> ORGANISM: Homo sapiens

```
<400> SEQUENCE: 36
caucacugga gcauaucug                                                19

<210> SEQ ID NO 37
<211> LENGTH: 19
<212> TYPE: RNA
<213> ORGANISM: Mus musculus

<400> SEQUENCE: 37
gaaagacucg cucuaauau                                                19

<210> SEQ ID NO 38
<211> LENGTH: 19
<212> TYPE: RNA
<213> ORGANISM: Mus musculus

<400> SEQUENCE: 38
auauuagagc gagucuuuc                                                19

<210> SEQ ID NO 39
<211> LENGTH: 19
<212> TYPE: RNA
<213> ORGANISM: Mus musculus

<400> SEQUENCE: 39
cuaugagacc guaauaaau                                                19

<210> SEQ ID NO 40
<211> LENGTH: 19
<212> TYPE: RNA
<213> ORGANISM: Mus musculus

<400> SEQUENCE: 40
auuuauuacg gucucauag                                                19

<210> SEQ ID NO 41
<211> LENGTH: 19
<212> TYPE: RNA
<213> ORGANISM: Mus musculus

<400> SEQUENCE: 41
ccauuauugu caucaaaga                                                19

<210> SEQ ID NO 42
<211> LENGTH: 19
<212> TYPE: RNA
<213> ORGANISM: Mus musculus

<400> SEQUENCE: 42
ucuuugauga caauaaugg                                                19

<210> SEQ ID NO 43
<211> LENGTH: 19
<212> TYPE: RNA
<213> ORGANISM: Mus musculus

<400> SEQUENCE: 43
aaguuagaau cuuccauaa                                                19

<210> SEQ ID NO 44
<211> LENGTH: 19
<212> TYPE: RNA
<213> ORGANISM: Mus musculus
```

```
<400> SEQUENCE: 44
uuauggaaga uucuaacuu                                              19
```

ALBUMIN PRODUCTION AND CELL PROLIFERATION

CROSS REFERENCE TO RELATED APPLICATIONS

This application is a continuation application of U.S. application Ser. No. 15/656,000 filed Jul. 21, 2017, entitled ALBUMIN PRODUCTION AND CELL PROLIFERATION, which is a divisional application of U.S. application Ser. No. 15/013,866 filed Feb. 2, 2016 entitled ALBUMIN PRODUCTION AND CELL PROLIFERATION, which is a divisional application of U.S. application Ser. No. 14/128,147 filed Dec. 20, 2013 entitled ALBUMIN PRODUCTION AND CELL PROLIFERATION, which is a national phase entry of PCT Application No. PCT/GB2012/051422 filed Jun. 20, 2012, which claims the benefit of priority of U.S. Application No. 61/499,637 filed Jun. 21, 2011, the contents of which are each incorporated herein by reference in their entirety.

REFERENCE TO SEQUENCE LISTING

The present application is being filed along with a Sequence Listing in electronic format. The sequence listing filed, entitled 2058-1007USDCON_SEQ_Listing.txt, was created on Mar. 8, 2018 and is 7,076 bytes in size. The information in electronic format of the Sequence Listing is incorporated herein by reference in its entirety.

FIELD OF THE INVENTION

The present invention relates to methods of up-regulating albumin production. The methods involve the use of short RNA molecules capable of increasing the expression of albumin. The invention also relates to the design and synthesis of such short RNA molecules and their use in therapy, such as treating hypoalbuminemia or cancer. Methods of inhibiting cell proliferation by up-regulating albumin production are also provided. Subject matter disclosed herein thus relates generally to short activating RNA (saRNA) and, in particular, saRNA for impacting cell proliferation.

BACKGROUND OF THE INVENTION

Current methods of up-regulating the expression of a gene of interest typically require the introduction of extra copies of the gene into a cell, either by using viruses to introduce extra copies of the gene into the host genome or by introducing plasmids that express extra copies of the target gene. By contrast, the present invention provides short activating RNA molecules which can upregulate gene expression, particularly albumin production.

Various studies indicate that short activating RNA (saRNA) can target a promoter region of a gene and activate the gene. Some have proposed a mechanism (Mechanism A) where short double-stranded or single stranded RNAs find a match in a promoter region of a gene to form a complex that binds to the promoter region and removes so-called "off" tags; and another mechanism (Mechanism B) where a cell produces RNA copies of a promoter region that somehow block production of a protein to silence a gene; and where short double-stranded or single stranded RNAs find a match to bind and destroy the RNA copies. These proposed mechanisms (e.g., believed to be one or possibly both) lead to turning "on" a target gene, for example, to provide for production of a protein. FIG. 1 shows approximate graphical diagrams that illustrate Mechanism A 110 (see graphics 112 and 114) and Mechanism B 120 (see graphic 122) with respect to a promoter region, a coding region and a double stranded RNA that can form a complex (see, e.g., Holmes, B., "Turn genes on, turn diseases off", New Scientist, 7 Apr. 2007, which is incorporated herein by reference).

RNA interference (RNAi) is an important gene regulatory mechanism that causes sequence-specific down-regulation of target mRNAs. RNAi is mediated by "interfering RNA" (iRNA); an umbrella term which encompasses a variety of short double stranded RNA (dsRNA) molecules which function in the RNAi process.

Exogenous dsRNA can be processed by the ribonuclease protein Dicer into double-stranded fragments of 19 to 25 base pairs, preferably 21-23 base pairs, with several unpaired bases on each 3' end forming a 3' overhang. Preferably, each 3' overhang is 1-3, more preferably 2, nucleotides long. These short double-stranded fragments are termed small interfering RNAs (siRNAs) and these molecules effect the down-regulation of the expression of target genes. Since the elucidation of their function, siRNAs have been used as tools to down-regulate specific genes.

A protein complex called the RNA-induced silencing complex (RISC) incorporates one of the siRNA strands and uses this strand as a guide to recognize target mRNAs. Depending on the complementarity between guide RNA and mRNA, RISC then destroys or inhibits translation of the mRNA. Perfect complementarity results in mRNA cleavage and destruction and as result of the cleavage the mRNA can no longer be translated into protein. Partial complementarity—particularly with sites in the mRNA's 3' untranslated region (UTR)—results in translational inhibition.

Recently it has been discovered that although RISC primarily regulates genes post transcription, RNAi can also modulate gene transcription itself. It is believed that short RNAs regulate transcription by targeting for destruction transcripts that are sense or antisense to the regulated RNA and which are presumed to be non-coding transcripts. Destruction of these non-coding transcripts through RNA targeting has different effects on epigenetic regulatory patterns depending on the nature of the RNA target. Destruction of ncRNA targets which are sense to a given mRNA results in transcriptional repression of that mRNA, whereas destruction of ncRNA targets which are antisense to a given mRNA results in transcriptional activation of that mRNA. By targeting such antisense transcripts, RNAi can therefore be used to up-regulate specific genes.

A published US patent application 2010/0210707 A1 ('707 application), which is incorporated by reference herein, sets forth some technology for use of saRNA. The '707 application describes selection of a non-coding region of a nucleic acid sequence of a gene to provide for complementarity of a saRNA strand to, in turn, provide for an increase in transcription of the corresponding gene. Such an approach infers that the "target" is known a priori. Further, the '707 application states explicitly "saRNAs do not target cryptic promoter transcription". In detail, the '707 application notes that expression of E-cadherin, p21 and GAPDH was detected using gene specific primer sets; that no cryptic transcript was detected using primers complementary to the E-cadherin promoter; and that no cryptic transcript was amplified in the p21 promoter.

The '707 application also describes an saRNA molecule with at least a first ribonucleic acid strand with a 5' region of complementarity to a non-coding sequence of a gene, where the gene encodes a polypeptide that inhibits cellular proliferation, and a 3' terminal region of at least one nucleotide non-complementary to the non-coding sequence, where administering of the saRNA provides for an increase in expression of the polypeptide and a decrease in cellular proliferation. As explicitly stated, the referred to polypeptide itself "inhibits cellular proliferation".

As described herein, various technologies, techniques, etc., can provide for saRNA, optionally without specific a priori knowledge, where such saRNA may be administered, directly or indirectly, to impact cell proliferation. In various examples, cell proliferation is impacted not by presence of a polypeptide that inhibits cell proliferation but rather by a controlling a mechanism (or mechanisms) for production of one or more polypeptides. As described herein, each of such one or more polypeptides may or may not, by presence of the polypeptide molecule itself, inhibit cell proliferation.

DETAILED DESCRIPTION

The present inventor has set out to provide a new method of upregulating albumin production in vivo or in vitro. He has developed new short RNAs which up-regulate albumin production. This up-regulation is achieved by up-regulating a target gene involved in albumin production. These RNAs activate gene expression, so they are also called short activating RNA (saRNA). The terms "short RNA" and "saRNA" are used interchangeably herein.

Without wishing to be bound by theory, it is believed that the short RNA molecules of the invention may act through mechanism A and/or B mentioned above. The short RNAs of the present invention may achieve modulation of the target gene by inducing the siRNA-like cleavage of the target RNA transcript which is antisense to a region of the target gene. Short RNAs of the present invention might also be able to act, in complex with Argonaute proteins, as anchors for regulatory chromatin-modifying proteins. The saRNA mechanism of action may involve chromatin remodelling, for example, through Polycomb group proteins. Polycomb group proteins can apparently directly interact with ncRNAs, including promoter-associated RNAs, and thereby be recruited to promoters and effect silencing. The saRNAs may therefore, by interfering with such Polycomb-recruiting ncRNAs, reduce Polycomb-levels at promoters and allow "positive" chromatin remodeling complexes such as Trithorax group proteins to establish positive histone marks.

Thus, the saRNA molecules may up-regulate albumin production via down-regulation of a target anti sense RNA transcript.

The inventor has used an advantageous method/algorithm for the identification of suitable RNA target transcripts and for the design of these saRNAs. The inventor has therefore provided novel short RNAs which target RNA transcripts in the host cell in order to upregulate target genes involved in albumin production.

The short RNAs of the invention are also referred to herein as "albumin production up-regulating" RNAs. Preferred features of the saRNAs of the invention are discussed below.

By a "target gene involved in albumin production", conveniently referred to herein as a "target gene", is meant a gene which when activated/upregulated results in increased albumin production. Albumin production may inter alia be upregulated using saRNAs which upregulate the albumin gene or saRNAs which upregulate the CEBPA gene, as shown in the Examples. Thus, the target gene may conveniently be the gene which encodes albumin (the "albumin gene"), in which case the saRNA may be said to have a direct effect. Alternatively, the target gene may encode a factor which immediately or ultimately regulates the production of albumin, in which case the saRNA may be said to have an indirect effect. Such a factor may for example be a transcription factor. Preferred examples include CEBPA and HNF4alpha.

Albumin is the body's predominant serum-binding protein. It has several important functions. It affects osmotic pressure, so when albumin no longer sustains sufficient colloid osmotic pressure to counterbalance hydrostatic pressure, oedema develops. Albumin transports various substances, including bilirubin, fatty acids, metals, ions, hormones, and exogenous drugs. It also affects platelet function.

CCAAT/enhancer binding protein alpha (CEBPA, also known as C/EBP alpha) is an intron-less gene which encodes a basic leucine zipper class of protein. The CEBPA protein consists of 2 N-terminal transactivation domains, a basic DNA binding domain and a C-terminal leucine zipper domain. CEBPA is a sequence specific, DNA binding protein purified initially from rat liver nuclei. The binding sites for CEBPA include CCAAT boxes and enhancer core homologies. It is capable of selectively integrating with cis-regulatory DNA sequences to positively control mRNA synthesis. Based on its ability to positively regulate cis-regulatory sequences, CEBPA is classed as a transcription factor.

CEBPA is expressed in a variety of tissues where it plays an important role in the differentiation of many cell types including adipocytes, type II alveolar cells and hepatocytes. In the mouse, CEBPA is found most abundantly in fat, liver and lung tissue. CEBPA is restricted further to terminally differentiated hepatic parenchymal cells. The functional role of CEBPA in liver cells was reported by Darnell et al., showing its regulation of alpha-1-antitrypsin, transthyretin and albumin. Furthermore expression of functional CEBPA in the liver cell line (HepG2) results in increased levels of cytochrome P450, a superfamily of monooxygenases that participates in the metabolism of endogenous substrates and plays a key role in detoxification and metabolic activation of key xenobiotics. CEBPA plays a physiologically relevant role in liver specific genes, as evidenced by its presence on the promoter element of the albumin gene.

HNF4A (hepatocyte nuclear factor 4 alpha) is a nuclear transcription factor that controls the expression of several genes. It binds as a homodimer, and may play a role in development of the liver, kidney, and intestines. HNF4A mutations are associated with monogenic autosomal dominant non-insulin-dependent diabetes mellitus type I.

Albumin production upregulation according to the present invention may be achieved by upregulating a single target gene, preferably selected from the target genes discussed above, or by upregulating at least 2 or at least 3 different target genes. Preferred combinations are upregulation of the albumin gene and the CEBPA gene; albumin gene and HNF4A gene; CEPBA gene and HNF4A gene; or albumin gene, CEBPA gene and HNF4A gene. Upregulation of any particular target gene may be achieved using a single saRNA (single or double stranded) or a combination of two or more different saRNAs (single or double stranded). When two or more target genes are upregulated, then a combination of at least one saRNA specific for the first target gene and at least one saRNA specific for the second target gene are used. Thus, at least 2, 3, 4, 5, 6, 7, 8, 9, 10, 11, 12, 13 or 14 different saRNAs may be used in any combination. Preferably, the saRNA comprises a first strand comprising or consisting of a sequence of SEQ ID NO: 5-36.

As discussed below, many conditions are characterised by hypoalbuminemia, so there is a need to increase albumin levels in patients suffering from such conditions. The present invention therefore provides new therapeutic approaches for the treatment of such conditions.

Surprisingly, the inventor has found that up-regulating albumin expression in a hyperproliferative cell inhibits proliferation of that cell and up-regulating albumin expression in vivo inhibits tumor development and growth, as shown in the Examples. This opens up new therapeutic approached for the treatment of hyperproliferative disorders.

As described herein, a cell may be modified by administration of a short activating RNA to thereby cause the cell to increase production of a molecule where production impacts cell proliferation. As an example, a hepatocyte is modified by administration of saRNA to increase production of albumin. In turn, the ability of the hepatocyte to divide (i.e., proliferate) is impacted negatively. In other words, the mechanism or mechanisms associated with the increase in production of albumin cause treated hepatocytes to exhibit reduced proliferation. As described herein, saRNA may be useful for treatment or prevention of cancer, such as primary liver cancer. For example, as to liver cancer, treatment or prevention may occur by administering saRNA to patients with liver cirrhosis (e.g., due to viral hepatitis or ethanol intoxication).

As an example, trials were undertaken with an objective of exploring the effect of up regulating albumin mRNA transcript on cell proliferation in the human hepatocellular carcinoma (HepG2) cell line. The trials included use of synthetic saRNA targeted at albumin, which was transfected into HepG2 using the Nanofectin liposomal method. For these trials, successful transfection was measured by an increase in mRNA levels in HepG2 cells. To demonstrate the impact, change in cellular proliferation was measured using tetrazolium salt, 4-[3-(4-iodophenyl)2-(4nitrophenyl)2H-5-tetrazolio]1,3benzene disulfonate (WST-1) proliferation assay.

These trials provided results that demonstrated that saRNA, targeted at the promoter region of the albumin gene, was successfully transfected into HepG2 cells (e.g., as albumin mRNA levels increased when compared to cells transfected with a scrambled RNA control). These results showed that cell proliferation markedly decreased only in cells that were reprogrammed to upregulate albumin expression. Such an effect was also observed in a human cell line expressing albumin. Also noted, for rat liver fibroblasts that do not express albumin, transfection of these rat cells with the same saRNAs, did not result in upregulation of albumin mRNA or a change in cell proliferation.

As described herein, enhancing albumin transcripts in HepG2 cells indirectly represses cell proliferation. In line with the established role that the transcription factors p53, HNF4-α, CEBPA-α and CEBPA-β have with albumin expression and induction of apoptosis; techniques, technologies, etc., described herein provide opportunities for targeting of hepatocarcinoma with saRNA molecules specific to albumin. More generally, as described herein, saRNA molecules can increase production of one or more molecules whereby the mechanism or mechanisms associated with production impact cell proliferation, to specifically reduce cell proliferation. Reduction in cell proliferation can be beneficial for treatment of various conditions.

Hepatocytes are generally perceived as being important for maintenance of several vital functions. For example, they can regulate carbohydrate and lipid metabolism and detoxification of exogenous and endogenous compounds. They can also produce plasma proteins such as albumin. Albumin is a typical liver-specific gene which is important for the transportation of particles through the body and the preservation of serum colloid osmotic pressure in the blood. The gene for albumin (albumin gene) is highly expressed in the liver after birth, and its regulation is transcriptionally controlled as indicated by the numerous factors that bind to the albumin promoter element (see, e.g., Panduro et al., 1987; Tilghman and Belayew, 1982). Several cis-acting elements in the albumin promoter exists (sites A-F). The B and D sites have been shown as to being important as liver-specific transcription factors bind to these elements (see, e.g., Maire et al., 1989). HNF-1 has been shown to bind to the B site (see, e.g., Courtois et al., 1988; Lichtsteiner and Schibler, 1989). Members of the C/EBP family which belong to the leucine zipper proteins of transcription factors have been shown to interact at the D site of the albumin promoter (see, e.g., Descombes et al., 1990; Landschulz et al., 1988; Mueller et al., 1990).

In general, several events may influence expression of the albumin gene. Under physiological conditions, extracellular oncotic pressure has been shown to controls albumin gene expression via HNF-1 (see, e.g., Pietrangelo et al., 1992; Pietrangelo and Shafritz, 1994). During pathological states, such as the acute phase response of the liver, albumin gene expression has been shown to be down-regulated (see, e.g., Trautwein et al., 1994). In recent years several transcription factors have been cloned which have shown involvement in the regulation of the acute phase genes. These include STAT3, C/EBP-β, IL6-DBP, NF-IL6, LAP or CRP2 (see, e.g., Akira et al., 1990; Akira et al., 1994; Cao et al., 1991; Chang et al., 1990; Descombes et al., 1990; Poli et al., 1990; Williams et al., 1991; Zhong et al., 1994). The C/EBP family of transcription factor is particularly relevant as members of this family bind to the D site of the albumin promoter and also regulates cell cycle arrest via p53 and HNF4-α (see, e.g., Barone et al., 1994; Buck et al., 1994; Johnson, 2005; Nagao et al., 1995). HNF4-α and CEBP-α have been both shown to be critical for liver function and differentiation (see, e.g., Hayhurst et al., 2001; Lee et al., 1997; Wang et al., 1995). Some studies have shown that transcriptional repression of both HNF4-α and CEBP by overexpression of the tumour suppressor p53 correlates with poor liver differentiation in cancer (see, e.g., Itoh et al., 2000; Nagao et al., 1995; Ng et al., 1995). An increase in p53 levels has been shown to correlate with a decrease in albumin expression possibly through inhibition of CEBP-α and β transcriptional activity (see, e.g., Kubicka et al., 1999). In normal conditions, wild type levels of p53 are very low and are increased only in response to cellular stress such as DNA damage, withdrawal of growth factors and hypoxia (see, e.g., Prives, 1998). Tight regulation of p53 protein level has been shown to be required to prevent blockage of the cell cycle and induction of apoptosis.

Albumin is not thought to have a role in cell proliferation, i.e. it is not involved in the cell cycle and not required for cell proliferation, nor are normal levels of albumin thought to affect cell proliferation. It can be contrasted with proteins such as cyclins and cyclin-dependent kinases which are involved in cell proliferation. Without wishing to be bound by theory, the inventor proposes that by upregulating albumin production, the cell's resources are diverted from cell proliferation and cell proliferation consequently slows down or steps entirely.

As described herein, as an example, upregulation of albumin (see FIG. 2) may be "tricking" cells into a reversion back to normal conditions where p53 levels are reduced-resulting in an increase in transcription of HNF4α, CEBPA-α and β- to restrict cell proliferation and growth (see, e.g., Maeda et al., 2002). Evidence from the trials demonstrate that upregulation of albumin by saRNA markedly represses proliferation of a liver cancer cell line (see FIG. 3).

Thus, in one aspect the present invention provides a method of treating or preventing a hyperproliferative disorder, comprising administering to a subject in need thereof a short activating RNA which up-regulates albumin production and thereby inhibits cell proliferation.

Alternatively viewed, the present invention provides a short activating RNA which up-regulates albumin production and thereby inhibits cell proliferation for use in therapy, preferably for use in treating or preventing a hyperproliferative disorder.

Also provided is an in vitro, ex vivo or in vivo method of inhibiting cell proliferation, comprising contacting a cell (sample), tissue (sample), organ or subject with a short activating RNA which up-regulates albumin production and thereby inhibits cell proliferation.

Also provided is a method of treating a subject having a condition characterised by hypoalbuminemia, comprising administering to said subject a short activating RNA which up-regulates albumin production.

Alternatively viewed, the present invention provides a short activating RNA which up-regulates albumin production for use in therapy, preferably for use in treating a disorder characterised by hypoalbuminemia.

Also provided is an in vitro, ex vivo or in vivo method of up-regulating albumin production by a cell, comprising contacting a cell (sample), tissue (sample), organ or subject with a short activating RNA which up-regulates albumin production.

In another aspect, the invention provides an saRNA capable of upregulating albumin production. Optional features of the saRNA molecules are described elsewhere herein.

The saRNAs of the invention may advantageously exert a dual effect, namely inhibit cell hyperproliferation and increase albumin levels. When administered to a subject suffering from a hyperproliferative disorder, the saRNAs not only reduce proliferation of the hyperproliferative cells, but they also increase albumin levels which may have a variety of positive outcomes such as improving liver function. When administered to a subject suffering from hypoalbuminemia, the saRNAs increase albumin levels and thereby alleviate the hypoalbuminemia, and they also help to prevent the development of a hyperproliferative disorder. A number of liver disorders, particularly cirrhosis, are characterised by hypoalbuminemia and particularly if left untreated typically increase the risk of the subject developing cancer. The present invention provides particularly advantageous treatments for such liver disorders, the treatments alleviating the hypoalbuminemia and reducing the risk of cancer. Thus, provided are saRNAs which simultaneously treat conditions characterised by hypoalbuminemia and hyperproliferative disorders.

"Capable of upregulating albumin production" means that the saRNA upregulates albumin production when inside a cell that has the necessary machinery for producing albumin and preferably naturally produces some albumin. Advantageously, upregulating albumin production inhibits cell proliferation, particularly hyperproliferation, so said saRNA is capable of inhibiting cell proliferation, particularly hyperproliferation. "Capable of inhibiting cell proliferation" means that the saRNA inhibits cell proliferation when inside a cell that has the necessary machinery for cell proliferation.

In another aspect, the invention provides an ex vivo or in vitro cell comprising an saRNA molecule of the invention.

In another aspect, the invention provides an ex vivo or in vitro cell in which albumin production has been upregulated by a method disclosed herein. Thus, such a cell is obtained or obtainable by the methods disclosed herein. Also provided is such a cell for use in therapy, preferably the treatment of a condition characterised by hypoalbuminemia, or any other type of liver disease.

A "hyperproliferative cell" may be any cell that is proliferating at a rate that is abnormally high in comparison to the proliferating rate of an equivalent healthy cell (which may be referred to as a "control"). An "equivalent healthy" cell is the normal, healthy counterpart of a cell. Thus, it is a cell of the same type, e.g. from the same organ, which performs the same functions(s) as the comparator cell. For example, proliferation of a hyperproliferative hepatocyte should be assessed by reference to a healthy hepatocyte, whereas proliferation of a hyperproliferative prostate cell should be assessed by reference to a healthy prostate cell.

By an "abnormally high" rate of proliferation, it is meant that the rate of proliferation of the hyperproliferative cells is increased by at least 20, 30, 40%, or at least 45, 50, 55, 60, 65, 70, 75%, or at least 80%, as compared to the proliferative rate of equivalent, healthy (non-hyperproliferative) cells. The "abnormally high" rate of proliferation may also refer to a rate that is increased by a factor of at least 2, 3, 4, 5, 6, 7, 8, 9, 10, or by a factor of at least 15, 20, 25, 30, 35, 40, 45, 50, or by a factor of at least 60, 70, 80, 90, 100, compared to the proliferative rate of equivalent, healthy cells.

Examples of hyperproliferative cells include cancerous cells (including carcinomas, sarcomas, lymphomas and blastomas). Such cancerous cells may be benign or malignant. Hyperproliferative cells may also result from an autoimmune condition such as rheumatoid arthritis, inflammatory bowel disease, or psoriasis. Hyperproliferative cells may also result within patients with an oversensitive immune system coming into contact with an allergen. Such conditions involving an oversensitive immune system include, but are not limited to, asthma, allergic rhinitis, eczema, and allergic reactions, such as allergic anaphylaxis.

The term "hyperproliferative cell" as used herein does not refer to a cell which naturally proliferates at a higher rate as compared to most cells, but is a healthy cell. Examples of cells that are known to divide constantly throughout life are skin cells, cells of the gastrointestinal tract, blood cells and bone marrow cells. However, when such cells proliferate at a higher rate than their healthy counterparts, then they are hyperproliferative.

A "hyperproliferative disorder" may be any disorder which involves hyperproliferative cells as defined above. Examples of hyperproliferative disorders include neoplastic disorders such as cancer, psoriatic arthritis, rheumatoid arthritis, gastric hyperproliferative disorders such as inflammatory bowel disease, skin disorders including psoriasis, Reiter's syndrome, *pityriasis rubra* pilaris, and hyperproliferative variants of the disorders of keratinization.

Cancer represents a hyperproliferative disorder of particular interest, and all types of cancers, including e.g. solid tumours and haematological cancers are included. Representative types of cancer include cervical cancer, uterine cancer, ovarian cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, endometrial cancer, plasmacytoma, lymphomas, retinoblastoma, Wilm's tumor, Ewing sarcoma, melanoma and other skin cancers. Liver cancer or prostate cancer are preferred. The liver cancer may include or consist of cholangiocarcinoma, hepatoblastoma, haemangiosarcoma, or hepatocellular carcinoma (HCC). HCC is of particular interest.

Preferably, tumour development and/or growth is inhibited. In a preferred embodiment, solid tumours are treated. In another preferred embodiment, metastasis is prevented.

By the "inhibition of cell proliferation" or "reduced proliferation" is meant that proliferation is reduced or stops altogether. Thus, "reducing proliferation" is an embodiment of "inhibiting proliferation". Proliferation of a cell is reduced by at least 20%, 30% or 40%, or preferably at least 45, 50, 55, 60, 65, 70 or 75%, even more preferably at least 80, 90 or 95% in the presence of the oligonucleotides of the invention compared to the proliferation of said cell prior to treatment with the oligonucleotides of the invention, or compared to the proliferation of an equivalent untreated cell. In embodiments wherein cell proliferation is inhibited in hyperproliferative cells, the "equivalent" cell is also a hyperproliferative cell. In preferred embodiments, proliferation is reduced to a rate comparable to the proliferative rate of the equivalent healthy (non-hyperproliferative) cell. Alternatively viewed, a preferred embodiment of "inhibiting cell proliferation" is the inhibition of hyperproliferation, or modulating cell proliferation to reach a normal, healthy level of proliferation.

The skilled person is fully aware of how to identify a hyperproliferative cell. The presence of hyperproliferative cells within an animal may be identifiable using scans such as X-rays, MRI or CT scans. The hyperproliferative cell may also be identified, or the proliferation of cells may be assayed, through the culturing of a sample in vitro using cell proliferation assays, such as MTT, XTT, MTS or WST-1 assays. Cell proliferation in vitro can also be determined using flow cytometry.

The cell proliferation assays listed above all work by the same principle; a stable tetrazolium salt is cleaved to form a soluble formazan by a complex cellular mechanism that occurs primarily at the cell surface. This bioreduction is largely dependent on the glycolytic production of NAD(P)H in viable cells. Therefore, the amount of formazan dye formed directly correlates to the number of metabolically active cells in the culture. Cells, grown in a tissue culture plate, are incubated with the reagent for approximately 0.5-4 hours. After this incubation period, the formazan dye formed is quantitated with a scanning multi-well spectrophotometer (ELISA reader). The measured absorbance directly correlates to the number of viable cells.

Tumor development or growth may be assayed using one or more known techniques, such as measurement of tumor size using an external caliper, calculation of tumor volume e.g. by use of the ellipsoid formula, computed tomography (CT), micro CT, positron emission tomography (PET), microPET, magnetic resonance imaging (MRI), immunohistochemistry and/or optical imaging such as bioluminescence imaging (BLI) or fluorescence imaging (FLI). In animal studies, once the animal has been sacrificed tumour volume may also be determined by measuring water displacement volume and tumour weight may be determined using scales.

The method of the present invention preferably reduces tumour volume, preferably by at least 10, 20, 30, 40, 50, 60, 70, 80 or 90%. Preferably, the development of one or more new tumours is inhibited, e.g. a subject treated according to the invention develops fewer and/or smaller tumours. By "fewer tumours" is meant that he develops a smaller number of tumours than an equivalent subject over a set period of time. Preferably, he develops at least 1, 2, 3, 4 or 5 fewer tumours than an equivalent control (untreated) subject. By "smaller" tumours is meant that the tumours are at least 10, 20, 30, 40, 50, 60, 70, 80 or 90% smaller in weight and/or volume than tumours of an equivalent subject.

The set period of time may be any suitable period, e.g. 1, 2, 3, 4, 5, 6, 7, 8, 9 or 10 months or years.

Preferably, the onset of cancer is prevented or delayed. This may be assessed by reference to an equivalent control (untreated) subject.

An "equivalent subject" may be e.g. a subject of similar age, sex and health such as liver health or cancer stage, or the same subject prior to treatment according to the invention. The equivalent subject is "untreated" in that he does not receive treatment with an saRNA according to the invention. However, he may receive a conventional anti-cancer treatment, provided that the subject who is treated with the saRNA of the invention receives the same or equivalent conventional anti-cancer treatment.

Albumin expression may be assayed through the use of well-established techniques that the skilled person would be well aware of. The up-regulation of the messenger RNA that encodes albumin may be determined using reverse transcriptase polymerase chain reaction (RT-PCR), preferably semi-quantitative or quantitative PCR (qRT-PCR). This method involves reverse transcribing the isolated mRNA into cDNA before carrying out real-time amplification cycles in the presence of a hybridization reporter probe for quantitative analysis. Albumin mRNA expression can also be determined using Northern blot analysis.

An up-regulation of the production of the albumin protein can be determined using an enzyme-linked immunosorbent assay (ELISA). This ELISA may be a sandwich ELISA, such as the AssayMax Albumin ELISA kit. Here, the sample is applied to a microplate that has been pre-coated with an antibody specific to albumin. After washing, which removes any non-albumin protein, the remaining albumin is sandwiched by using another specific antibody. Excess antibody is washed before a secondary antibody is applied which has a detectable label. Protein expression can also be determined using Western blot analysis or protein mass spectrometry.

By "up-regulating albumin expression", it is meant that the expression of the albumin protein is increased by at least 20, 30, 40%, more preferably at least 45, 50, 55, 60, 65, 70, 75%, even more preferably at least 80% in the presence of the saRNA oligonucleotides of the invention compared to the expression of albumin in the absence of the saRNA oligonucleotide. In a further preferable embodiment, the expression of the albumin protein is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of the saRNA oligonucleotides of the invention compared to the expression of albumin in the absence of the saRNA oligonucleotide. In another preferred embodiment, the up-regulation would relate to both the synthesis and the processing of the serum albumin protein into its active form.

The upregulation of albumin production may be assayed by reference to albumin expression by the test cell prior to treatment with the saRNAs of the invention, or by reference to albumin expression by an equivalent untreated cell (control).

Preferably, the methods of the invention also result in secretion of albumin, more preferably in increased secretion of albumin. Preferably, intracellular albumin levels and/or serum levels of albumin are increased.

In some embodiments, the methods of the invention result in upregulation of the expression of CEBPA and/or HNF4A, but in other embodiments, the methods of the invention result in downregulation of CEBPA and/or HNF4A.

In some embodiments, the methods of the invention result in downregulation of α fetoprotein and/or hepatocyte growth factor.

In some embodiments, the methods disclosed herein may include a step of assaying cell proliferation and/or assaying albumin production before and/or after administration of the saRNA to a subject. For example, the methods may include a step of determining that albumin expression has increased and/or that proliferation of hyperproliferative cells, e.g. cancer cells, has decreased as a result of a treatment according to the present invention.

Hypoalbuminemia is a condition where albumin within blood serum is insufficient or abnormally low. There are many conditions that are characterised by hypoalbuminemia, including conditions which cause hypoalbuminemia and conditions which are the cause of hypoalbuminemia. Such conditions include, but are not limited to, liver diseases, such as hepatitis B and C, viral infections of the liver, alcoholic liver disease such as fatty liver, liver cirrhosis or alcoholic hepatitis, conditions that cause an excessive level of albumin to be excreted, such as nephrotic syndrome, conditions that cause albumin to be lost through the bowels, such as Menetrier's disease, burns patients, who lose albumin through plasma loss, and conditions that cause a redistribution of albumin, such as oedema. Such conditions may benefit from increased levels of albumin, which may be provided by the saRNA oligonucleotides of the invention.

An insufficient level of albumin is defined by a level of albumin that falls outside the levels considered healthy for that animal. For example, in humans, an insufficient level of albumin would be considered as a level below 38 g/L or 35 g/L, or even below 32 or 30 g/L.

Liver disease or poor liver function is thus typically characterised by hypoalbuminemia, so it may be useful to assess liver function to determine whether a subject may benefit from a therapy provided by the present invention. Liver function assessments may also provide a useful way of determining the success of a particular treatment.

Methods that may be used to diagnose a diseased liver that may benefit from the treatments of the invention, or to determine the success of a particular treatment, are well known in the art. Liver function tests may be carried out through analysing a blood sample obtained from an animal. Proteins that would be quantified in such liver function tests may include bilirubin, aspartate aminotransferase (AST), alanine aminotransferase (ALT), alkaline phosphatase (ALP), gamma glutamyl transpeptidase (GGT), total protein and globulin protein, as well as serum albumin. These proteins may be referred to as "liver function markers" or "liver health markers". Below is a Table that shows the healthy ranges of the above proteins in humans.

TABLE 3

| Protein | Minimum concentration | Maximum concentration |
| --- | --- | --- |
| Bilirubin | 0 μmol/L | 20 μmol/L |
| AST | 0 U/L | 45 U/L |

TABLE 3-continued

| Protein | Minimum concentration | Maximum concentration |
| --- | --- | --- |
| ALT | 0 U/L | 45 U/L |
| ALP | 30 U/L | 120 U/L |
| GGT | 0 U/L | 45 U/L |
| Total Protein | 60 g/L | 80 g/L |
| Globulin Protein | 20 g/L | 32 g/L |
| Serum Albumin | 38 g/L | 55 g/L |

Many of the above proteins are not liver-specific indicators of disease. However, elevated GGT alone usually indicates some form of liver disease. When some of the protein levels are analysed in combination, they can be an accurate means of determining specific liver diseases. For example, an elevated GGT, a decrease in ALT and a decrease in ALP in combination could be an indication of alcoholic liver disease or fatty liver disease. An elevated GGT, an elevated ALT and a decrease in ALP in combination could be an indication of hepatitis, but can also be an indication of fatty liver disease.

In some embodiments, the methods of the invention include a step of diagnosing a liver disease/diagnosing that a subject may benefit from an saRNA or cell of the invention. Said step may comprise carrying out one or more of these liver function tests. Alternatively or in addition, the methods may include a step of analysing liver function after administration of the saRNA or cell of the invention. Said step may comprise carrying out one or more of these liver function tests. Preferably, after said treatment an improvement in at least one of said liver function markers is determined.

For example, at least 1 of bilirubin, AST, ALT, ALP and GGT may show a decrease that is 1, 2, 3, 4 or 5 fold, or an increase by at least 10, 20, 30, 40, 50, 60, 70, 80 or 90%. Preferably, at least 2, 3, 4 or all of these markers show such a decrease. Thus, the methods of the invention preferably result in a blood bilirubin concentration of less that 20, 15, 10 or 5 μmol/L; a blood AST concentration of less than 45, 40, 30, 25, 20, 15, 10 or 5 U/L; a blood ALT concentration of less than 45, 40, 30, 25, 20, 15, 10 or 5 U/L; a blood GGT concentration of less than 45, 40, 30, 25, 20, 15, 10 or 5 U/L; and/or a blood ALP concentration of less than 120, 100, 80, 70, 60, 50 or 40 U/L, but preferably no less than 30 U/L.

The methods of the invention preferably result in a blood albumin concentration of at least 32, 34, 35, 37, 38, 39, 40, 41, 42, 43, 44, 45, 46, 47, 48, 49 or 50 g/L, e.g. 38-55, 40-55, 42-55, 45-55 g/L.

Effective treatments according to the present invention may mean that the disease that is being treated, be that one involving hyperproliferative cells or hypoalbuminemia, is cured. However, an effective "treatment" encompasses any outcome which is of benefit to the patient, be it temporary or permanent. The treatment may affect the underlying condition, and/or it may affect the symptoms. Thus, purely symptomatic relief is also contemplated.

Prevention according to the present invention means that the prophylactic administration of the saRNA oligonucleotides or cells of the present invention prevents, reduces the risk of, or delays the onset of the development a condition characterised by hyperproliferative cells or an insufficient level of albumin. Such prophylactic administration may be used for patients that are at risk of developing a condition characterised by hyperproliferative cells or hypoalbuminemia. Prophylactic administration may be effective over the lifetime of the patient. However, prophylactic administration may also need to be repeated over the lifetime of the patient, or until the condition that puts the patient at risk can be alleviated.

In the methods of the invention, cells are contacted with a short RNA molecule of the present invention. The cells may be in vitro, e.g. an established cell line or a sample having previously been obtained from a subject, or they may be in vivo in a subject. The short RNA molecules can be administered to cells in vitro or in vivo by using any suitable delivery reagents in conjunction with the present short RNAs. Such suitable delivery reagents include the Minis Transit TKO lipophilic reagent; lipofectin; lipofectamine; cellfectin; or polycations (e.g., polylysine), virus-based particles, electroporation dendrimers or liposomes. A preferred delivery reagent is a liposome. A variety of methods are known for preparing liposomes.

Another preferred deliver reagent is a dendrimer. Dendrimers are described in Singha et al. (2011), *Nucleic Acid Ther.* 21:133, the entire disclosure of which is herein incorporated by reference. Dendrimers are regular and highly branched macromolecules. Preferably, the dendrimer is a polycationic dendrimer, such as PAMAM dendrimers. Without wishing to be bound by theory, PAMAM dendrimers bear primary amine groups on their surface which facilitate nucleic acid binding, and contain tertiary amino groups which enhance the release of the nucleic acid in the cytoplasm.

The step of contacting cells with saRNAs may also be referred to as "transfection".

Particularly preferably, the liposomes encapsulating the present short RNAs are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Recombinant plasmids which can express the short RNAs can also be administered directly or in conjunction with a suitable delivery reagent, including the Minis Transit LT1 lipophilic reagent; lipofectin; lipofectamine; cellfectin; polycations (e.g., polylysine) or liposomes. Recombinant viral vectors which express the short RNA and methods for delivering such vectors to a cell are known within the art.

Preferably said contacting step is performed more than once, preferably every 3 days, although it may also be daily, or every 2, 4 or 5 days. The contacting is preferably performed for at least 1, 2, 3, 4, 5, 6, 7, 8, 9, 10, 11, 12, 13, 14 or 15 days, about 6 or 9 days being preferred. Contacting at regular intervals over a period of weeks or months is also contemplated.

In the methods disclosed herein, if more than one target gene is up-regulated then the short RNAs used to up-regulate the different target genes may be administered at different frequencies and for different lengths of time. The particular administration regimens to be used can be readily determined by one of ordinary skill in the art to suit his desired purpose, particular starting cell type and delivery method. By way of example, picoMolar concentrations of the short RNA molecules of the present may be used.

The short RNA of the invention may be provided alone or in combination with other active agent(s) known to have an effect in the particular method being considered. The other active agent(s) may be administered simultaneously, separately or sequentially with the short RNA of the invention. Thus, it is possible to use a single short RNA of the invention, a combination of two or more short RNAs of the invention or a combination of said short RNA(s) and other active substance(s).

The methods of the invention are preferably carried out on cells or subjects that are animal, more preferably mammalian, e.g. mouse, rat, monkey, dog, cow, sheep, most preferably human, although optionally the cell or subject is non-human. The cell or subject may be embryonic, but is preferably adult.

It must be appreciated that the methods of the inventions may not, and indeed need not, achieve the upregulation of albumin production in all of the cells within a population of cells that is contacted with an saRNA of the invention. Thus, out of a population of cells subjected to the method of the present invention, i.e. contacted with an saRNA of the invention, preferably at least 10, 20, 30, 40, 50, 60, 70, 80 or 90%, may be induced to produce more albumin, although in some embodiments albumin production is up-regulated in at least 95 or 99% of the cells.

In vitro and in vivo methods may be carried out using (i) a cell which naturally produces albumin, such as a hepatocyte; (ii) a cell which has the potential to differentiate into a cell which naturally produces albumin, such as a stem cell; or (iii) a cell which does not normally produce albumin, such a somatic non-liver cell. Hepatocytes or stem cells are preferred. The stem cell may be totipotent, pluripotent or multipotent, e.g. Haemopoietic stem cells (HSC), mesenchymal stem cells (MSC) or induced pluripotent stem cells.

WO2005/059113 discloses a particularly advantageous type of pluripotent stem cell. This stem cell can be directly isolated from bone marrow and/or blood, e.g. peripheral blood, or from material taken from the umbilical cord or placenta, and has the unique ability to differentiate into ectodermal, mesodermal and endodermal cells. These cells are thus clearly multipotent or pluripotent, if not totipotent. Therefore, the stem cells described in WO2005/059113 provide a useful source of cells for tissue transplantation that may be used in an autologous (self-to-self) manner.

The cells disclosed in WO2005/059113 are known in the art as "OmniCytes". The teachings of WO2005/059113 are incorporated herein in their entirety by reference. OmniCytes are stem cells which are CD34+, capable of self regeneration and capable of differentiation into ectodermal, mesodermal and endodermal cells, including haemopoietic cells. As mentioned above, they can be directly isolated from bone marrow and/or blood. They are further characterised by their ability to adhere to plastic (e.g. the plastic of standard tissue culture vessels) during culturing. Suitable vessels are those manufactured by Corning Incorporated, New York, USA.

OmniCytes may be further characterised by the fact that they do not require feeder layers, i.e. cells (typically inactivated by gamma irradiation which supply important metabolites without further growth or division of their own) which support the growth of the stem cells.

OmniCytes can be further characterised as obtainable by:
a) enrichment of a tissue or blood sample for $CD34^+$ cells;
b) contacting the sample with a solid support and harvesting the cells which adhere to said solid support.

Suitable tissue or blood samples include, bone marrow, peripheral blood, umbilical cord blood or tissue, placenta and samples obtained from liposuction.

More particularly, they are obtainable by:
subjecting a tissue or blood sample (preferably haemopoietic tissue such as blood or a bone marrow sample) to density gradient separation;

exposing low density cells to an affinity ligand for CD34 (preferably attached to paramagnetic beads);
recovering cells attached to said CD34 ligand;
exposing the CD34+ subpopulation to tissue culture grade plastic; and
recovering CD34+ cells adherent to the plastic.

Omnicytes are preferably adult, so non-foetal.

A sample of OmniCytes was deposited with ECACC at Porton Down, Salisbury, SP4 0JG on 24 Sep. 2004 under accession number 04092401. The deposit was made by Professor Myrtle Gordon of Willow Tree Cottage, Spinning Wheel Lane, Binfield, Berkshire RG42 5QH, Great Britain and the cell line was given the name "Stem Cell OmniCyte". On 14 Jun. 2012 Professor Myrtle Gordon authorised Mina Therapeutics Limited to refer to the deposited biological material in any and all patent applications, and she gave her unreserved and irrevocable consent to the deposited material being made available to the public in accordance with Rule 33 EPC.

As set out in the Examples, the methods of the invention allow the generation of cells which produce albumin. More specifically, they produce more albumin than their untreated counterparts, so they overproduce albumin, or they are cells that do not typically produce albumin but which have been induced to produce albumin. Thus, in a further aspect there is provided a cell which produces or overproduces albumin. The cell is obtainable by the methods disclosed herein. Preferably, the cell is obtained by inducing a CD34+ stem cell such as an OmniCyte to produce albumin.

The cell is preferably ex vivo, i.e. not part of a living organism. Optionally, the cell may be referred to as "in vitro" or "isolated".

Uses of such cells in therapy represents a further aspect of the invention.

Optionally, the cell of the present invention and saRNA of the present invention may be used in combination in the therapeutic applications disclosed herein. "In combination" includes separate, simultaneous or sequential administration.

Alternatively viewed, the present invention provides a method of treatment comprising administering to a subject in need thereof a therapeutically effective amount of an albumin-producing cell and/or a therapeutically effective amount of an saRNA as defined herein.

The saRNAs may be designed to be complementary to a target transcript, and they may exert their effect on albumin production by down-regulating a target antisense RNA transcript.

The target RNA transcript is preferably transcribed from a locus up to 100, 80, 60, 40, 20 or 10 kb upstream of the target gene's transcription start site, or from a locus up to 100, 80, 60, 40, 20 or 10 kb downstream of the target gene's transcription stop site. Optionally, the RNA transcripts are transcribed from a locus up to 1 kb upstream of the target gene's transcription start site or from a locus up to 1 kb downstream of the target gene's transcription stop site. Optionally, the RNA transcripts are transcribed from a locus up to 500, 250 or 100 nucleotides upstream of the target gene's transcription start site or from a locus up to 500, 250 or 100 nucleotides downstream of the target gene's transcription stop site, more preferably the locus is no more than 500 nucleotides upstream or downstream from the target gene's transcription start site. Most preferably the target RNA transcript is transcribed from a locus up to 500 nucleotides upstream or up to 500 nucleotides downstream of the target gene's transcription start site.

The term "is transcribed from [a particular locus]" in the context of the target RNA transcripts of the invention means "the transcription start site of the target RNA transcript is found [at the particular locus]". Preferably both of the transcription start site and the transcription stop site of the target RNA transcript are, separately, located either up to 100 kb upstream of the target gene's transcription start site or up to 100 kb downstream of the target gene's transcription stop site. The preferred embodiments described above in relation to the location from which the target RNA transcript is transcribed apply mutatis mutandis to the location of the target RNA transcript's transcription stop site.

The target RNA transcript is complementary to the coding strand of the genomic sequence, and any reference herein to "genomic sequence" is shorthand for "coding strand of the genomic sequence".

Thus, the target RNA transcript comprises a sequence which is antisense to a genomic sequence located between 100, 80, 60, 40, 20 or 10 kb upstream of the target gene's transcription start site and 100, 80, 60, 40, 20 or 10 kb downstream of the target gene's transcription stop site. More preferably, the target RNA transcript comprises a sequence which is antisense to a genomic sequence located between 1 kb upstream of the target gene's transcription start site and 1 kb downstream of the target gene's transcription stop site. More preferably, the target RNA transcript comprises a sequence which is antisense to a genomic sequence located between 500, 250 or 100 nucleotides upstream of the target gene's transcription start site and ending 500, 250 or 100 nucleotides downstream of the target gene's transcription stop site. Optionally the target RNA transcript comprises a sequence which is antisense to a genomic sequence which includes the coding region of the target gene. Most preferably, the target transcript comprises or consists of a sequence which is antisense to a genomic sequence that overlaps with the target gene's promoter region. Thus, the target RNA transcript preferably comprises a sequence which is antisense to the promoter region.

Genes may possess a plurality of promoter regions, in which case the target RNA transcript may overlap with one, two or more of the promoter regions. Online database of annotated gene loci may be used to identify the promoter regions of genes.

For any given promoter region, the entire promoter region does not have to be overlapped, it is sufficient for a subsequence within the promoter region to be overlapped by the target RNA transcript, i.e. the overlap can be a partial overlap. Similarly, the entire target RNA transcript need not be antisense to the sequence within the promoter region, it is only necessary for the target RNA transcript to comprise a sequence which is antisense to the promoter region.

The region of overlap between the target RNA transcript and the promoter region of the target gene may be as short as a single nucleotide in length, although it is preferably at least 15 nucleotides in length, more preferably at least 25 nucleotides in length, more preferably at least 50 nucleotides in length, more preferably at least 75 nucleotides in length, most preferably at least 100 nucleotides in length. Each of the following specific arrangements are intended to fall within the scope of the term "overlap":

a) The target RNA transcript and the target gene's promoter region are identical in length and they overlap (i.e. they are complementary) over their entire lengths.

b) The target RNA transcript is shorter than the target gene's promoter region and overlaps over its entire length with the target gene's promoter region (i.e. it is complementary over its entire length to a sequence within the target gene's promoter region).

c) The target RNA transcript is longer than the target gene's promoter region and the target gene's promoter region is overlapped fully by it, i.e. the target gene's promoter region is complementary over its entire length to a sequence within the target RNA transcript).

d) The target RNA transcript and the target gene's promoter region are of the same or different lengths and the region of overlap is shorter than both the length of the target RNA transcript and the length of the target gene's promoter region.

The above definition of "overlap" applies mutatis mutandis to the description of other overlapping sequences throughout the description. Clearly, if an antisense RNA transcript is described as overlapping with a region of the target gene other than the promoter region then the sequence of the transcript is complementary to a sequence within that region rather than within the promoter region.

Preferably the RNA transcript comprises a sequence which is antisense to a genomic sequence which comprises the target gene's transcription start site. In other words, preferably the target RNA transcript comprises a sequence which overlaps with the target gene's transcription start site.

The target RNA transcript is preferably at least 1 kb, more preferably at least 2, 3, 4, 5, 6, 7, 8, 9 or 10, e.g. 20, 25, 30, 35 or 40 kb long.

The term "sense" when used to describe a nucleic acid sequence in the context of the present invention means that the sequence has identity to a sequence on the coding strand of the target gene. The term "antisense" when used to describe a nucleic acid sequence in the context of the present invention means that the sequence is complementary to a sequence on the coding strand of the target gene.

The "coding strand" of a gene is the strand which contains the coding sequence for the gene's mRNA. The "template strand" of a gene is the strand which does not contain the coding sequence for the gene's mRNA.

Preferably the target RNA transcript comprises a sequence which is at least 75%, preferably at least 85%, more preferably at least 90%, still more preferably at least 95% complementary along its full length to a sequence on the coding strand of the target gene.

The present invention provides saRNA molecules which can effectively and specifically down-regulate such target transcripts. This can be achieved by the saRNA molecules having a high degree of complementarity to a sequence within the target RNA transcript. The short RNA will have no more than 5, preferably no more than 4 or 3, more preferably no more than 2, still more preferably no more than 1, most preferably no mismatches with a region of a target RNA transcript.

Preferably, the saRNA comprises a sequence of at least 13 nucleotides which has at least 95, 98, 99 or 100% complementarity to a region of the target transcript. Preferably, said sequence which has at least 95, 98, 99 or 100% complementarity to a region of the target transcript is at least 15-20, e.g. at least 15, 16, 17, 18 or 19 nucleotides in length, preferably 18-22 or 19 to 21, most preferably exactly 19. As mentioned elsewhere, the saRNA may also comprise a 3' tail.

In one embodiment, the short RNA molecules of the present invention may have siRNA-like complementarity to a region of the target transcript; that is, 100% complementarity between nucleotides 2-6 from the 5' end of the guide strand in the saRNA duplex and a region of the target transcript. Other nucleotides of the short RNA molecule may, in addition, have at least 70, 80, 90, 95, 99 or 100% complementarity to a region of the target transcript. For example, nucleotides 7 (counted from the 5' end) until the 3' end may have least 70, 80, 90, 95, 99 or 100% complementarity to a region of the target transcript.

The sequence within the target RNA transcript to which the saRNA molecules of the present invention preferably have a high degree of complementarity is preferably antisense to a genomic sequence that is up to 500 nucleotides upstream or downstream of the target gene's transcription start site. Preferably, it overlaps the target gene's promoter.

The skilled person will appreciate that it is convenient to define the saRNA by reference to the target transcript, regardless of the mechanism by which the saRNA upregulates albumin production. However, the saRNA may alternatively be defined by reference to the target gene. The target transcript is complementary to a genomic region on the coding strand of the target gene, and the saRNA is in turn complementary to a region of the target transcript, so the saRNA may be defined as having sequence identity to a region on the coding strand of the target gene. All of the features discussed herein with respect to the definition of the saRNA by reference to the target transcript apply mutatis mutandis to the definition of the saRNA by reference to the target gene so any discussion of "complementarity" to the "target transcript" should be understood to include "identity" to the "genomic sequence". Thus, the saRNA preferably has a high percent identity, e.g. at least 75, 80, 85, 90, 95, 98 or 99, preferably 100% identity, to a genomic sequence surrounding the target gene's transcription start site. The distances that the genomic sequence may have from the TSS are discussed above. It is preferable that the genomic sequence is up to 500 nucleotides upstream or downsteam of the TSS. Most preferably, it overlaps the target gene's promoter. Thus, the saRNA preferably has sequence identity to a sequence that overlaps the promoter region of the target gene.

Preferably the "short" RNA molecule of the invention is from 13 nucleotides to 30 nucleotides in length, preferably from 15 or 17 to 30 nucleotides, more preferably 16 to 25 nucleotides in length, still more preferably 17 to 21 nucleotides in length, most preferably 19, 20, 21 or 22 nucleotides in length. In other words, the short RNA molecules may comprise a first strand of a length discussed above. If a 3' tail is present, the strand may be longer, preferably 19 nucleotides plus a 3' tail, which is preferably UU or UUU.

The short RNA molecule may be single or, preferably, double stranded. Double stranded molecules comprise a first strand and a second strand. If double stranded, preferably each strand of the duplex is at least 14, more preferably at least 18, e.g. 19, 20, 21 or 22 nucleotides in length. Preferably the duplex is hybridised over a length of at least 12, more preferably at least 15, more preferably 17, still more preferably at least 19 nucleotides. Each strand may be exactly 19 nucleotides in length. If a 3' tail is present, the strand may be longer, preferably 19 nucleotides plus a 3' tail, which is preferably UU or UUU.

Preferably the duplex length is less than 30 nucleotides since duplexes exceeding this length may have an increased risk of inducing the interferon response. The strands forming the dsRNA duplex may be of equal or unequal lengths.

Most preferably the short RNA molecule is a short interfering RNA (siRNA) molecule.

Optionally the short RNA molecules are dsRNA molecules which consist of the two strands stably base-paired together with a number of unpaired nucleotides at the 3' end of each strand forming 3' overhangs. The number of unpaired nucleotides forming the 3' overhang of each strand is preferably in the range of 1 to 5 nucleotides, more preferably 1 to 3 nucleotides and most preferably 2 nucleotides. The 3' overhang may be formed of the 3' tail mentioned above, so the 3' tail may be the 3' overhang.

All references to sequence complementarity or identity used herein refer to the whole length of the short RNA molecule unless specifically stated otherwise.

The short RNA may include a very short 3' or 5' sequence which is not complementary to the target RNA transcript. Preferably, such a sequence is 3'. Said sequence may be 1-5 nucleotides in length, preferably 2-3, e.g. 2 or 3. Said sequence preferably comprises or consists of uracil, so most preferably it is a 3' stretch of 2 or 3 uracils. This non-complementary sequence may be referred to as "tail". Thus, the short RNA preferably consists of (i) a sequence having at least 95% complementarity to a region of the target RNA; and (ii) a 3' tail of 1-5 nucleotides, which preferably comprises or consists of uracil residues. The short RNA will thus typically have complementarity to a region of the target RNA transcript over its whole length, except for the 3' tail, if present. As mentioned above, instead of "complementary to the target RNA transcript" the saRNA may be defined as having "identity" to the coding strand of the relevant genomic sequence.

Preferred sequences of suitable saRNAs of the invention are provided in Table 1. Thus, provided are short RNAs having a first strand comprising or consisting of a sequence selected from SEQ ID NOs: 6, 8, 10, 12, 14, 16, 18, 20, 22, 24, 26, 28, 30, 32, 34 and 36. Optionally, the short RNA may comprise a 3' tail at the 3' end of any of these sequences.

Single stranded short RNA molecules only consist of a first strand, whereas double stranded short RNA molecules also have a second strand. The short RNAs may thus have a second strand comprising or consisting of a sequence selected from SEQ ID NOs: 5, 7, 9, 11, 13, 15, 17, 19, 21, 23, 25, 27, 29, 31, 33 and 35.

A short RNA having a first strand of SEQ ID NO:14 and a second strand of SEQ ID NO: 13 was shown to be particularly effective in treating cancer, so this is particularly preferred.

Table 1 indicates preferred pairings, each row representing a preferred pairing. Thus, for example, the short RNA preferably has a first strand comprising or consisting of a sequence of SEQ ID NO: 14, optionally with a 3' tail, and a second strand or consisting of a sequence of SEQ ID NO: 13 optionally with a 3' tail.

Any of the short RNA sequences disclosed herein may optionally include such a 3' tail. Thus, any of the sequences disclosed in the Tables may optionally include such a 3' tail.

As used herein, the term "RNA" means a molecule comprising at least one ribonucleotide residue. By "ribonucleotide" is meant a nucleotide with a hydroxyl group at the 2' position of a beta-D-ribo-furanose moiety. The terms include double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the RNA or internally, for example at one or more nucleotides of the RNA. Nucleotides in the RNA molecules of the present invention can also comprise non-standard nucleotides, such as non-naturally occurring nucleotides or chemically synthesized nucleotides or deoxynucleotides. These altered RNAs can be referred to as analogs or analogs of naturally-occurring RNA.

The term "double stranded RNA" or "dsRNA" as used herein refers to a ribonucleic acid duplex.

The term "short interfering RNA" or "siRNA" as used herein refers to a nucleic acid molecule capable of modulating gene expression through RNAi via sequence-specific-mediated cleavage of one or more target RNA transcripts. Typically, in RNAi the RNA transcript is mRNA and so cleavage of this target results in the down-regulation of gene expression. In this invention however, up-regulation or down-regulation of the target gene can be achieved by cleavage of RNA transcripts which are antisense or sense to the target gene of interest respectively.

By "complementarity" and "complementary" are meant that a first nucleic acid can form hydrogen bond(s) with a second nucleic acid for example by Watson-Crick base pairing. A nucleic acid which can form hydrogen bond(s) with another nucleic acid through non-Watson-Crick base pairing also falls within the definition of having complementarity. A percent complementarity indicates the percentage of residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary).

By "identity", "identical" or "sequence identity" is meant that a first nucleic acid is identical in sequence to a second nucleic acid sequence. A percent identity indicates the percentage of residues in a first nucleic acid molecule that are identical to a second nucleic acid sequence (e.g., 5, 6, 7, 8, 9, 10 out of 10 being 50%, 60%, 70%, 80%, 90%, and 100% identical).

Sequence alignments and percent identity or percent complementarity calculations may be determined using any method or tool known in the art including but not limited to the Megalign program of the LASARGENE bioinformatics computing suite (DNASTAR Inc., Madison, W1), the Clustal V method of alignment (Higgins and Sharp (1989) CABIOS. 5:151-153) and the BLAST 2.0 suite of programs. Software for performing BLAST analyses is publicly available, e.g., through the National Center for Biotechnology Information. The skilled man will be able to set the parameters of these tools to suit his desired purpose.

When assessing the identity or complementarity of a first and second nucleic acid sequence wherein one sequence is a DNA sequence and the other is an RNA sequence, it must be borne in mind that RNA sequences comprise uracil whereas DNA sequences would comprise thymine instead. Therefore, in these instances when assessing sequence identity, a uracil residue is considered to be identical to a thymine residue and when assessing complementarity a uracil residue is considered to be complementary to/capable of forming hydrogen bonds with an adenine residue.

The determination of the degree of complementarity of two or more sequences can be performed by any method known in the art. Preferably, the method used is that set out in Hossbach et al. (supra). In accordance with this method, the Perl script accessible at http://www.mpibpc.mpq.de/groups/luehrmann/siRNA is used.

In addition, various tools for the design and analysis of short RNA molecules are well-known, which permit one of ordinary skill in the art to determine those RNA molecules which can achieve effective and specific down-regulation of a target RNA transcript. Established methods include, for example, the GPboost and Reynolds algorithms (PMIDs:

15201190, 14758366). In addition, the ability of a short RNA to cause effective down-regulation of a target RNA can be evaluated using standard techniques for measuring the levels of RNA or protein in cells. For example, a short RNA of the invention can be delivered to cultured cells, and the levels of target RNA can be measured by techniques including but not limited to Northern blot or dot blotting techniques, or by quantitative RT-PCR.

Preferably the short RNAs possess none of the motifs aaaa, cccc, gggg, or uuuu. Preferably the short RNAs have a GC-percentage of at least 20% and no more than 75%, i.e. between 20% and 75%, preferably between 20% and 55%. The short RNAs of the above methods are ideally thermodynamically stable duplexes, in which case the GC percentage of each strand is at least 25% and no more than 75%, i.e. between 25% and 75%, preferably between 20% and 55%.

Tools and algorithms for determining whether or not RNAs possess the motifs aaaa, cccc, gggg or uuuu and for determining the percentage GC content of the molecules/strands are well known to the skilled artisan. Such tools include those described and referenced in Saetrom and Snove, (2004) *Biochem Biophys Res Commun* 321: 247-253 and Vert et al., (2006) *BMC Bioinformatics* 7: 520 (17 pages).

Short RNAs can induce down-regulation of non-target transcripts that have a limited number of mismatches to the short RNA strand which is incorporated into the RISC protein complex. This reduces the efficiency of the short RNA molecule and is therefore not desired. Consequently, short RNA molecules should have limited complementarity to transcripts other than the intended target to prevent unintended off-target effects. The probability of a short RNA candidate having cleavage-based off-target effects is a function of its complementarity to non-target RNA sequences and can be determined by any known method in the art. Optionally, an ungapped Smith-Waterman method (T F Smith & M S Waterman (1981) *Journal of molecular biology* 147: 195-197) can be used to screen the candidate short RNA against the Ensembl (Flicek, P., et al. (2008) *Ensembl* 2008. *Nucleic Acids Res* 36: D 707-714) human transcriptome database (Snøve, O., Jr., et al. (2004) *Biochem Biophys Res Commun* 325: 769-773) to identify a short RNA's potential off-target transcripts. Alternatively, the short RNA can be screened against a population of chosen RNA sequences, for example a selection of GenBank sequences, which do not encompass the entire Ensembl human transcriptome database. Alternatively, a Hamming distance measure can be used.

Preferably, the short RNA molecules have more than two mismatches to the identified off-target transcripts. Alternatively viewed, preferably the short RNA molecules have a Hamming distance of 2 or greater to all potential off-target transcripts. If the short RNA is double stranded then preferably both strands satisfy this requirement.

Optionally, the short RNA molecules have characteristics in common with known highly effective standard siRNAs. Preferably, the short RNA, or if double stranded one or both strands of the short RNA, has a GPboost score of more than 0.1. GPboost is a known genetic programming-based prediction system of siRNA efficacy and the methods used for determining the GPboost score of siRNA strands is disclosed in "Predicting the efficacy of short oligonucleotides in antisense and RNAi experiments with boosted genetic programming", Pal Saetrom (2004) *Bioinformatics* 20(17): 3055-3063, the content of which is incorporated here by reference. Alternatively or in addition, the short RNA molecules possess specific sequence features which are associated with highly effective siRNAs. The algorithm described by Reynolds [Reynolds et al. (2004) *Nature biotechnology* 22(3):326-330], which is incorporated here by reference permits the determination of whether or not short RNAs possess sufficient features of this type. One of ordinary skill in the art would be able to define and refine his threshold for his particular purpose.

Optionally, the short RNA molecules contain position-specific sequence motifs which are associated with highly effective siRNAs. siRNA efficacy prediction algorithms are well-known in the art and motifs which are associated with highly-effective siRNAs are discussed in Saetrom and Snove, (2004) *Biochem Biophys Res Commun* 321: 247-253, the content of which is incorporated here by reference.

Preferably the short RNA molecule is capable of direct entry into the RNAi machinery of a cell or is capable of being processed by Dicer before entry into the RNAi machinery of a cell. Methods of determining whether or not a short RNA molecule is capable of being processed by Dicer before entry into the RNAi machinery of a cell are well-known in the art, for instance in vitro Dicer assays such as that disclosed in Tiemann et al. (2010) *RNA* 16(6): 1275-1284 and Rose et al. (2005) *Nucleic Acid Research* 33(13):4140-4156.

If the short RNA molecule is double stranded and if only one strand within the molecule is capable of effectively and specifically down-regulating the target RNA transcript then preferably that strand is preferentially loaded into RISC. The design of double-stranded RNA molecules in which one strand is preferentially loaded into RISC is within the competence of one of ordinary skill in the art. For instance, the 5' end of the strand of the short RNA molecule which targets the target RNA transcript can be made or selected to be less thermodynamically stable than the 5' end of the other strand. Preferably there is a large difference in duplex thermodynamic end stability such that the 5' end of the strand of the short RNA molecule which targets the target RNA transcript is less thermodynamically stable than the 5' end of the other strand. The absolute value of the difference in duplex thermodynamic end stability ($\Delta\Delta G$) can be calculated in accordance with any method standard in the art. Optionally, the absolute value of the difference in duplex thermodynamic end stability is calculated by RNAfold (Hofacker et al., (2003) *Nucleic Acids Research* Vol. 31, No. 13, pp 3429-3431) by considering the 5 closing nucleotides at the ends of the duplex. Preferably the absolute value of the difference in duplex thermodynamic end stability as calculated by RNAfold is more than 0 kcal/mol, more preferably more than 1 kcal/mol, more preferably more than 3 kcal/mol.

Many standard tools for short RNA design, such as those described above, provide means for assessing this property of the molecules. For instance, double-stranded molecules can be selected if they have thermodynamic properties which favour the incorporation of one strand over the other into the RNAi machinery. Alternatively, the preferential loading of one strand can be achieved by using dsRNAs which contain RNA that differs from naturally-occurring RNA by the addition, deletion, substitution and/or alteration of one or more nucleotides.

Methods of determining the target RNA transcripts present in a cell are well-known in the art. For instance, the genomic region around the locus of the gene of interest can be searched for spliced expresses sequence tags. An expressed sequence tag or EST is a short sub-sequence of a transcribed cDNA sequence. ESTs are commonly used to identify gene transcripts. Public databases of ESTs are known in the art, for instance the GenBank database. Alternatively, Reverse Transcriptase PCR (RT-PCR), a well-known tool for identifying RNA, can be used to identify potential target RNA transcripts. Alternatively, high throughput sequencing or other such methods can be used to sequence total, size-fractionated, or other suitable subsets of RNAs and use such sequencing libraries to identify RNA transcripts that originate from the region of interest. Alternatively, a population of known RNA transcripts can be searched to identify suitable transcripts. Any database of RNA transcripts known in the art can be used, for instance the University of California Santa Cruz (UCSC) Spliced EST track. Alternatively, the population may be prepared from a population possessed by the skilled man working the invention for his own specific purposes. For instance, if the target gene is known to be expressed in a particular cell type, then the database of transcripts may be those which have been determined to be present in that cell type. The skilled man will be able to determine the population to use for his specific desired purposes.

However, for the purpose of the present invention the positive identification of any RNA transcripts which are antisense to the target gene is not in fact required. Thus, the existence of said non-coding RNA transcript (i.e. the target transcript to be down-regulated) need not be determined. The present inventor found that if the nucleotide sequence of the coding strand of the gene in the region surrounding the gene's transcription start site is obtained, i.e. determined by sequencing or found on a database, and the reverse complementary RNA sequence to that region is determined, then short RNA molecules which are complementary to that latter sequence can be used to up-regulate the target gene. Complementarity requirements are discussed elsewhere herein. The region surrounding the gene's transcription start site is the region located between 100, 200, 300, 400, 500, 800, 1000 or 2000 nucleotides upstream and downstream of the transcription start site.

Thus, the saRNA molecules may be designed based on the principles set out above. In some embodiments, the approach described below may be taken.

For example, FIG. 4 shows a block diagram of a method 400. In the method 400, a selection block 410 includes selecting a gene sequence of a gene for purposes of designing one or more short activating RNA molecules. Preferred genes are discussed elsehwere herein. In a provision block 420, the method 400 includes providing information such as information about a target genomic location, orientation and transcriptional structure (e.g., from a database). In an identification block 430, identification of one or more antisense transcripts occurs (e.g., searching data for transcripts that are antisense to and in the vicinity of the target gene), although it not necessary to actually determine the existence of a non-coding RNA transcript. In a provision block 440, the method 400 includes providing a bounded region about a transcription start site (TSS). For example, a number of units on one side and a number units on another side of a TSS may be provided as a bounded region. In a design process commencement block 450, the method 400 may commence a computer-aided process that acts to facilitate to design one or more saRNAs. Such a process may rely on one or more techniques selected from, for example, statistical techniques, genetic programming (GP) techniques, boosting techniques, neural network techniques, hidden Markov model (HMM) techniques, vector machine (SVM) techniques, etc. In general, such techniques provide for designing one or more saRNAs when provided a bounded TSS region as an input.

In the example of FIG. 4, the method 400 also includes an output block 460, which can output one or more designed saRNAs and optionally call for or actively take one or more steps to construct one or more saRNAs. As to output, the block 460 may output information to a display, a printer, memory, an interface, etc. For example, the block 460 may output information to a network via a network interface, output information to a machine configured for chemical processing to construct molecules, etc.

Also shown in FIG. 4 are various devices 412, 422, 432, 442, 452 and 462, which may be storage media configured to store instructions for performing one or more actions of the associated blocks 410, 420, 430, 440, 450 and 460. For example, the blocks 412, 422, 432, 442, 452 and 462 may be one or more computer-readable media that include information such as processor- or computer-executable instructions. While shown individually, a single storage medium may include instructions for more than one of the blocks 412, 422, 432, 442, 452 and 462. A storage medium may be a hard drive, an optical disk, memory (e.g., a memory card), etc.

As described herein, one or more computer-readable media can include computer-executable instructions to instruct a computing system to receive information (e.g., as in block 420), to identify antisense transcripts (e.g., as in block 430), to identify a bounded region for a transcription start site (e.g., as in block 440) and to call for commencement of a saRNA design process (e.g., as in block 450). Such one or more computer-readable media may optionally include instructions to instruct a computing system to design one or more saRNAs. Further, one or more computer-readable media may include instructions to cause a computing system to write or transmit one or more designed saRNAs. For example, information about one or more saRNAs may be written to a storage medium, transmitted via an interface (e.g., a network interface), etc. Accordingly, a machine configured for constructing one or more saRNAs may receive such information and subsequently construct such one or more saRNAs (e.g., as in block 460). As another example, consider a scenario where one or more saRNAs are available from one or more sources. As described herein, a search of such one or more sources may occur to identify one or more available saRNAs (e.g., consider a catalog, a saRNA bank, etc.).

As described herein, in various trials, the gene sequence for human albumin was selected (see, e.g., block 410). Such a gene sequence was selected for designing short activating RNA molecules for its specific activation where four parameters were used: 1) targeting gene annotations from UCSC RefSeq database; 2) targeted sequence from antisense RNA; 3) promoter selection of antisense sequences; and 4) identification of candidate short activating RNAs. Next, downloading of information occurred for the target's genomic location, orientation, and transcriptional structure from one or more available databases (e.g., RefSeq at UCSC) (see, e.g., block 420).

Next, given the database of RNA transcripts with known read direction, such as the UCSC Spliced EST track, searching the database occurred for transcripts that are antisense to and in the vicinity of the target gene (see, e.g., block 430). More specifically, a process included identifying antisense transcripts that (a) overlap the target's promoter and the target mRNA's 5' end; (b) overlap the target mRNA; (c) are at most 20-100 kb upstream of the target's transcription start site (TSS); or (d) are at most 20-100 kb downstream of the target's poly-adenylation site. A process can use these four criteria as hierarchical filters such that if it finds antisense transcripts that for example satisfy criterion (a), the process does not necessarily need to consider the three other criteria.

Next, based on the target's transcription start site (TSS), a process can include downloading the antisense genomic sequence from, for example, a fixed size region upstream and downstream of the TSS. In various trials, a typical region size used was 500 nts upstream and downstream of TSS, but larger or smaller sizes may be suitably implemented (see, e.g., block 440).

Following the downloading, a process may include designing one or more siRNAs that give effective and specific down-regulation of the antisense target sequence (see, e.g., block 450). For example, a process may (a) use a siRNA design algorithm, such as GPboost, to identify candidate effective siRNAs; (b) remove all candidate siRNAs with aaaa, cccc, gggg, or uuuu motifs and GC content less than 20% or greater than 55%; (c) remove all candidates that have Hamming distance less than two to all potential off-target transcripts; and (d) return a given number of remaining non-overlapping siRNAs sorted by their predicted siRNA knockdown efficacy. In such an example, the process can return a number (e.g., the two highest scoring) of saRNAs for a given antisense target sequence. As described herein, output and construction of one or more saRNA followed (see, e.g., block 460).

The saRNAs of the invention can be produced by any suitable method, for example synthetically or by expression in cells using standard molecular biology techniques which are well-known to the skilled artisan. For example, the saRNAs can be chemically synthesized or recombinantly produced using methods known in the art.

As mentioned above, the saRNAs and/or cells may be used therapeutically. The saRNAs or cells may be administered via injection, e.g. intravenously, subcutaneously, intramuscular or into a target organ. Thus, injection may be systemic or at or into the target site, e.g. a target organ, preferably the liver, although the prostate or pancreas is also contemplated. Alternatively, administration may be oral or pr (per rectum). Injection of a cell into the liver is preferred.

The short RNAs and/or cells of the invention may be administered to a patient in need thereof by any means or delivery vehicle known in the art, for example via nanoparticles, cationic lipids, lipids such as cholesterol or α-tocopherol, liposomes, e.g. positively charged cationic liposomes, polymers, such as polyethyleneimine, dendrimers, aptamers, or as antibody conjugates. The short RNAs may also be administered as viral vector expressed shRNAs or miRNA mimics.

Preferably, the saRNA or cell is associated, e.g. complexed with, linked to, or contained within, a moiety that targets the saRNA or cell to a specific tissue or cell type, e.g. liver cells, e.g. hepatocytes. Said moiety may be one of the means/delivery vehicles mentioned above. However, targeted delivery may not in fact be required, because drugs and particularly saRNAs are naturally delivered to the liver following systemic administration.

Aptamers are oligonucleotides or peptides with high selectivity, affinity and stability. They assume specific and stable three-dimensional shapes, thereby providing highly specific, tight binding to target molecules. For any specific molecular target, nucleic acid aptamers can be identified from combinatorial libraries of nucleic acids, e.g. by a technique called systematic evolution of ligands by exponential enrichment (SELEX) (see, for example, Tuerk C and Gold L: Systematic evolution of ligands by exponential enrichment: RNA ligands to bacteriophage T4 DNA polymerase. Science 1990, 249:505-510.). Peptide aptamers may be identified e.g. using a yeast two hybrid system. The skilled person is therefore able to design suitable aptamers for delivering the saRNAs or cells of the present invention to target cells such as liver cells. DNA aptamers, RNA aptamers and peptide aptamers are contemplated. Administration of short RNAs of the invention to the liver using liver-specific aptamers is particularly preferred.

Also provided is a conjugate of an aptamer and an short RNA of the invention. The conjugate may be formed using any known method for linking two moieties, such as direct chemical bond formation, linkage via a linker such as streptavidin and so on.

Methods of generating antibodies against a target cell surface receptor are well known. The saRNA molecules of the invention may be attached to such antibodies, for example using RNA carrier proteins. The resulting complex may then be administered to a subject and taken up by the target cells via receptor-mediated endocytosis. The cells of the invention may be linked to such antibodies using known means.

The saRNA or cells may be encapsulated in liposomes using methods known in the art. The liposomes may optionally be associated with a target-cell specific moiety such as an antibody or a peptide.

As discussed above, the molecules of the present invention are generated based on sequence analysis of a target gene and methods and products associated with delivery of these short nucleic acid molecules are further aspects of the invention. Thus, the present invention also provides methods and products, including computer-readable storage media and data structures, which may be set out schematically in FIG. 4-FIG. 9 and are discussed below with reference to FIG. 4-FIG. 9. Unless otherwise stated, the definitions, description and preferred embodiments described above in relation to the methods and products of the present invention apply, mutatis mutandis, to the aspects discussed below.

BRIEF DESCRIPTION OF THE DRAWINGS

The following examples are intended to be illustrative of the present invention and to teach one of ordinary skill in the art to make and use the invention. These examples are not intended to limit the invention in any way. The invention will now be further described in the following Examples and the Tables and Figures.

A more complete understanding of the various methods, devices, assemblies, systems, arrangements, etc., described herein, and equivalents thereof, may be had by reference to the following detailed description when taken in conjunction with examples shown in the accompanying drawings where:

FIG. 1 is a diagram of some possible mechanisms (Mechanism A and Mechanism B);

FIG. 3A and FIG. 3B are a series of plots of for WST-1 proliferation assay results in HepG2 cells following saRNA transfection. See Table 1 for the sequences of albumin PR1, PR2, PR3 and PR4;

FIG. 6 is a block diagram of an example of a method;

FIG. 10A: mouse albumin ELISA results comparing HepG2 cells transfected with saRNA specific to albumin against control HepG2 cells. *=p(0.0136). FIG. 10B: qPCR analysis of albumin mRNA, comparing HepG2 cells transfected with saRNA specific to albumin against control HepG2 cells. **=p(<0.003). FIG. 10C: qPCR analysis of albumin mRNA, comparing rat liver epithelial cells transfected with saRNA specific to albumin against control rat liver epithelial cells.

FIG. 11A shows the relative mRNA transcript levels of CEBPA, FIG. 11B shows the relative mRNA transcript levels of albumin, FIG. 11C shows albumin expression (ng/ml) and FIG. 11D shows HepG2 cell viability.

FIG. 12A shows the relative mRNA transcript levels of CEBPA, FIG. 12B shows the relative mRNA transcript levels of albumin and FIG. 12C shows HepG2 cell viability.

FIG. 16A shows the relative mRNA transcript levels of α feto protein (AFP) and FIG. 16B shows the relative mRNA transcript levels of hepatocyte growth factor (HGF).

Table 1 shows short RNA molecules designed for upregulating albumin expression.

Table 2 shows short RNA molecules designed for upregulating albumin expression.

Figures 2A, 2B:
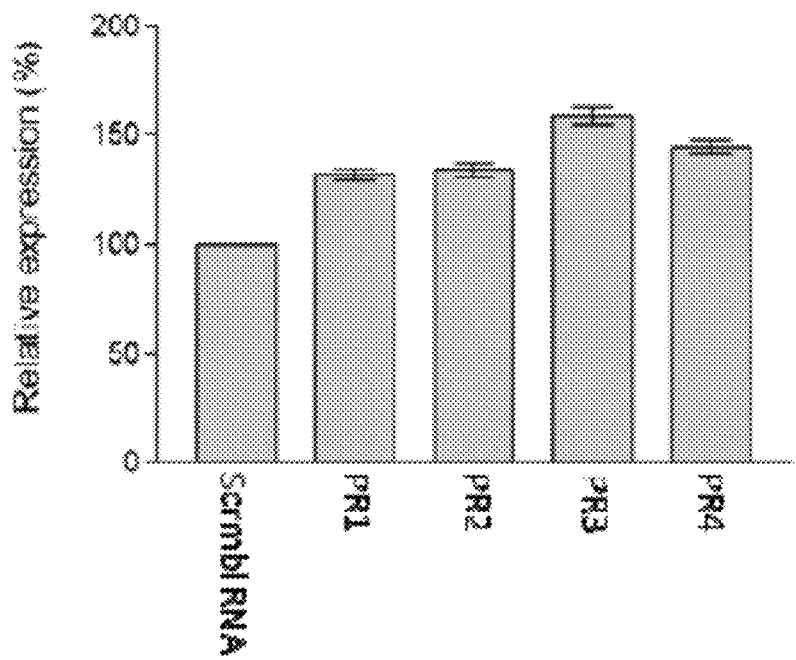
FIG. 2A and FIG. 2B are a series of plots of results for saRNA transfected HepG2 cells demonstrating upregulation of albumin. See Table 1 for the sequences of albumin PR1, PR2, PR3 and PR4.

More specifically, FIG. 2A-2B show a plot of data as to saRNA transfected HepG2 cells to demonstrate upregulation of albumin. In FIG. 2A represents a plot of results from HepG2 cells that were plated at a density of $2.5 \times 10^5$ cells/well in a 24 well plate. Four clones of saRNA were directed at the promoter regions (PR1, PR2, PR3 and PR4) of the albumin gene were used. Cells were transfected with 150 ng of saRNA at 0, 12 and 24 hours following plating in a 24 well plate followed by harvesting for extraction of total RNA. An RT-PCR profile of the mRNA levels showed an increase in albumin levels only in cells transfected with saRNAs. In FIG. 2B represents a plot of results from a semi-quantitative analysis from two independent trials to show that PR3 saRNA had the most marked increase in albumin mRNA level (158%+/5.7%). As to FIG. 3, results from a WST-1 proliferation assay are shown in HepG2 cells following saRNA transfection. HepG2 cells were plated at a density of $1.5 \times 10^5$ cells/well in a 24 well followed by three transfections at 0, 12 and 24 hours. WST-1 reagent was then added for 30 minutes before analysis in a multiplate reader at Amax450 nm. In FIG. 3A is a plot that presents the amount of formazan dye, indicative of metabolically active and proliferative cells, which was drastically reduced only in cells that were transfected with saRNA to albumin. In FIG. 3B is a plot that presents the percentage of cell viability relative to untransfected cells to demonstrate that cells transfected with PR3 saRNA had the most marked decrease in cell proliferation.

As to details of various trials described herein, specifically as to cell culture, HepG2 cells (American Type Culture Collection) were cultured in RPMI-140 media (Sigma, USA) supplement with 10% fetal calf serum (FCS) (Invitrogen, USA), 100 units/ml penicillin, 0.1 mg/ml streptomycin, 2 mmol/L glutamine (Sigma, USA) at 37° C. in humidified 5% CO2 air.

As to chemical processing, for various trials, paired saRNA oligonucleotides were annealed using 50 mM Tris-HCl, pH8.0, 100 mM NaCl and 5 mM EDTA following a denaturation step at 90° C. followed by a gradual anneal step to room temperature.

A process of isolation of total RNA for semiquantitative rtPCR can include various acts. For example, all total RNA extraction can be carried out using the RNAqueous-Micro kit (Ambion, UK) (e.g., following the manufacturer's instructions). As to various trials, cells were gently centrifuged followed by 3 pulses of sonication at Output 3 in Lysis buffer (Ambion, UK). The cell lysates were then processed through an RNA binding column, followed by multiple washes and elution. The total RNA isolated was quantified by a Nanodrop 2000 spectrophotometer. 500 ng of total RNA was reversed transcribed using One Step RT-PCR (Qiagen, Germany) (e.g., following the manufacturer's instructions). Expression for albumin and for loading control, a house keeping gene actin was performed by PCR using their respective primer pairs: albumin-F: TCC AGC ACT GCC TGC GGT GA; R: TCC GTC ACG CAC TGG GAG GA; following 37 cycles at 95° C.—45 sec; 55° C.—45 sec; 61° C.—45 sec. Actin-F: GAG AAA ATC TGG CAC CAC ACC; R: ATA CCC CTC GTA GAT GGG CAC following 37 cycles at 95° C.—5 min; 60° C.—30 sec; 70° C.—45 sec; 72° C.—10 min at 37 cycles. Products were analyzed in triplicate semi quantitatively using UVP VisonWorks LS (v6.2.).

For trials described herein, the tetrazolium salt, 4-[3-(4-iodophenyl)2-(4nitrophenyl)2H-5-tetrazolio]1,3benzene disulfonate (WST-1)-proliferation assay was used. Specifically, HepG2 ($1.5 \times 10^5$ cells/well) were plated in a 96 well plate and cultured in 500 ul of RPMI-140 media (Sigma, USA) supplement with 10% fetal calf serum (FCS) (Invitrogen, USA), 100 units/ml penicillin, 0.1 mg/ml streptomycin, 2 mmol/L glutamine (Sigma, USA) were transfected using Nanofectin (transfection of 150 ng of annealed saRNA targeted to MafA using Nanofectamine (PAA, UK) (e.g., following the manufacturer's instructions). The foregoing process was repeated three times at 0 hr, 12 hr and 24 hr from plating. The cell proliferation reagent WST-1 (Roche Applied Science, UK) was added (e.g., following the manufacturer's instructions). The colorimetric assay was then incubated for 30 minutes to allow cleavage of the tetrazolium salt WST-1 to a formazan dye by mitochondrial succinate-tetrazolium reductase in viable cells. The quantity of formazan dye, which is directly related to the number of metabolically active cells proliferating was measured at Amax450 nm in a multiwall plate reader. For trials, a total of three independent experiments were assayed.

Again, as shown in FIGS. 2A-2D and 3A-3B, saRNA transfected HepG2 cells demonstrated upregulation of albumin and WST-1 proliferation assay results, in HepG2 cells following saRNA transfection, demonstrated reduced proliferation.

Figure 4:
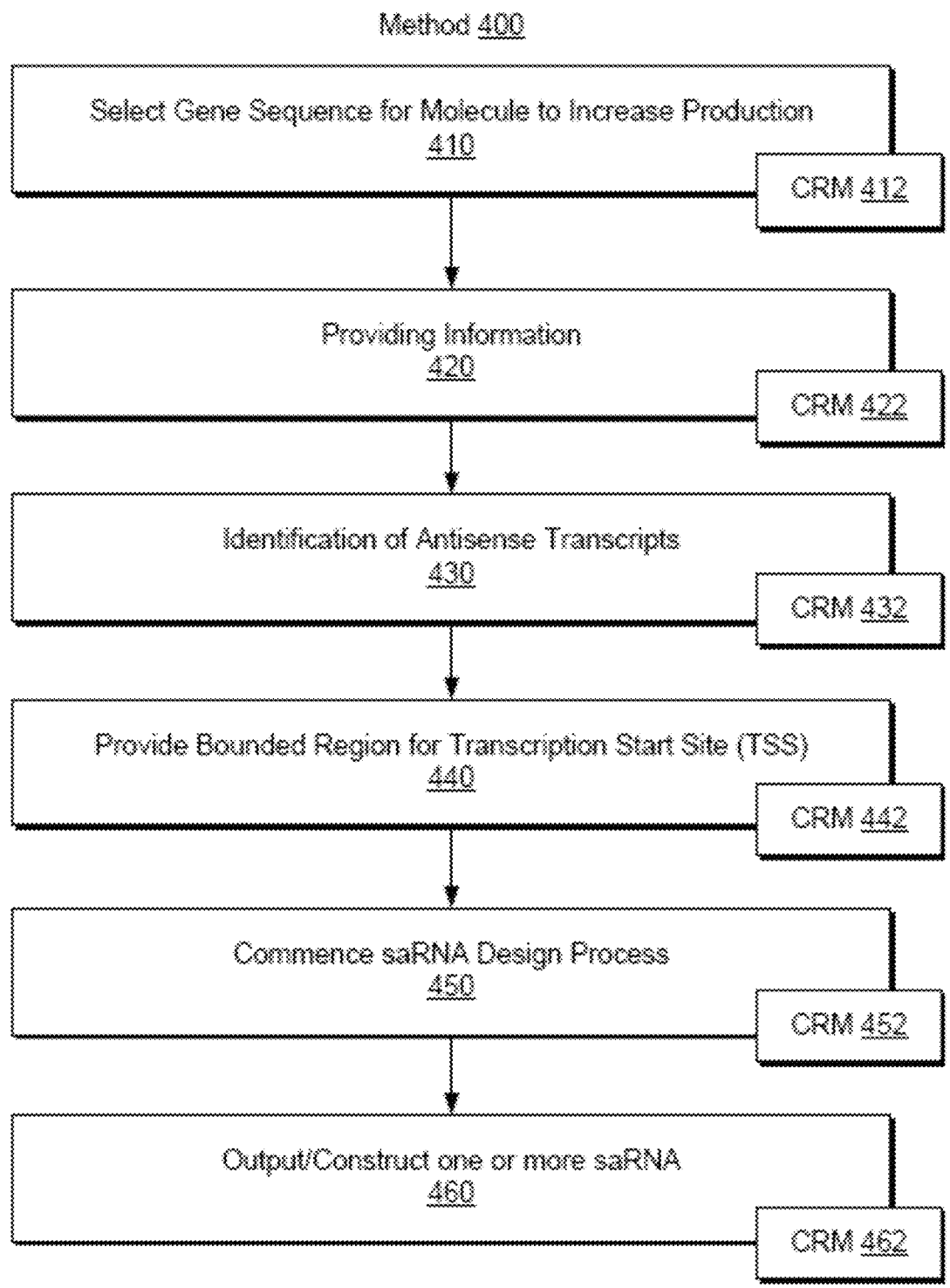
FIG. 4 is a block diagram of an example of a method.
Figure 5:
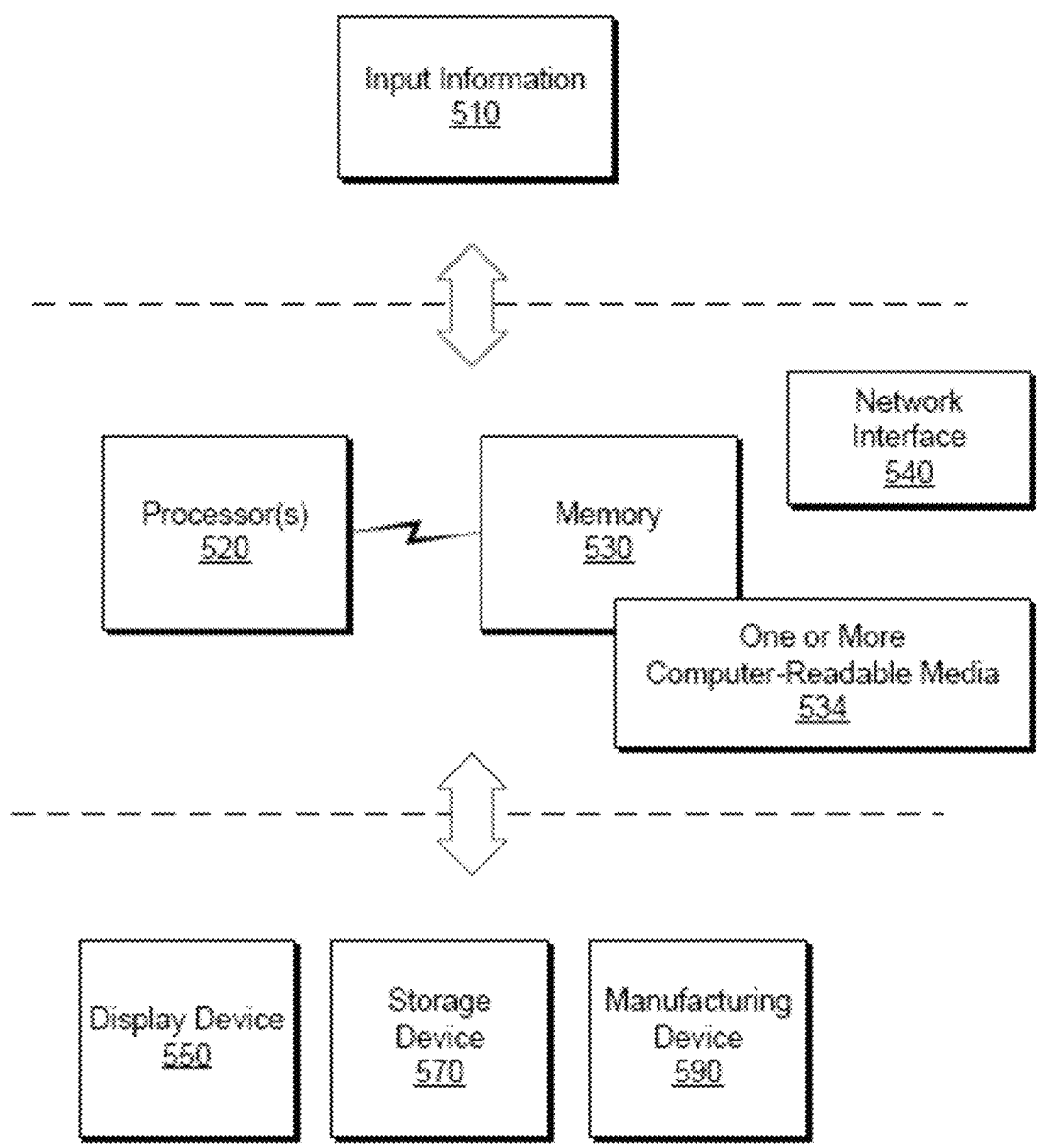
FIG. 5 is a block diagram of examples of equipment and a computing device.

FIG. 5 shows a system 500 (e.g., a computing system) that may include various components. In the example of FIG. 5, the system 500 may include input information 510, which may be provided to processor(s) 520 and memory 530, for example, via a network interface 540 or other interface. As shown, a CRM block 534 may include one or more computer-readable media. Such medium or media may be one or more of those of FIG. 4 (see, e.g., 412, 422, 432, 442, 452 and 462). Also shown in FIG. 5 is a display device 550, a storage device 570 and a manufacturing device 590.

As described herein, the manufacturing device 590 may include one or more chemicals (e.g., one or more probes, optionally one or more other chemicals such as an enzyme, etc.) and optionally vessels, wells, etc., for holding one or more chemicals.

In the example of FIG. 5, the system 500 can include one or more processors 520 operatively coupled to memory 530, which may be configured to store instructions read from one or more computer-readable (or processor-readable) storage media 534. As described herein, the CRM 534 may store instructions that, upon execution by the one or more processors instruct the system 500 to perform at least part of the method 400 of FIG. 4.

Also shown in the example of FIG. 5 is the network interface 540, which may allow for communication of information to or from the system 500. For example, instructions may be communicated to the system 500 (e.g., to commence operation, terminate operation, quality control, update software instructions, etc.). Output of the processor(s) 520 may be communicated from the system 500 via the network interface 540 (e.g., to a healthcare provider, a scientist, a database, a manufacturer of pharmaceuticals, etc.).

FIG. 6 shows a block diagram of a method 600. As mentioned, saRNA may be useful for treatment or prevention of cancer, such as primary liver cancer. For example, as to liver cancer, treatment or prevention may occur by administering saRNA to patients with liver cirrhosis (e.g., due to viral hepatitis or ethanol intoxication). The method 600 includes a diagnosis block 610 for diagnosing a patient condition, a provision block 620 for providing saRNA and an administration block 630 for administering the provided saRNA to the patient. As described herein, such actions may occur, wholly or partially, via a machine or machines, optionally operating based on instructions such as instructions stored on one or more computer-readable media (see, e.g., CRM 612, 622 and 632).

The method 600 of FIG. 6 may be performed in conjunction with one or more block of the method 400 of FIG. 4. For example, the provision block 620 may include designing as described with respect to the block 450 of the method 400 FIG. 4.

As to the diagnosis block 610, it may provide for diagnosing cancerous cells 611, diagnosing pre-cancerous cells 613, diagnosing other risk 615 or any combination thereof. As mentioned, certain conditions pose risks for cancer. For example, patient infections, patient habits, patient intoxication, etc., can pose risks for cancer. As described herein, a method can include inputting information, assessing risk based at least in part on the information and deciding whether to administer RNA to a patient or patients similarly situated. Such administration (e.g., or administrations) may be, for example, for prevention of cancer or treatment of cancer.

Figure 7:
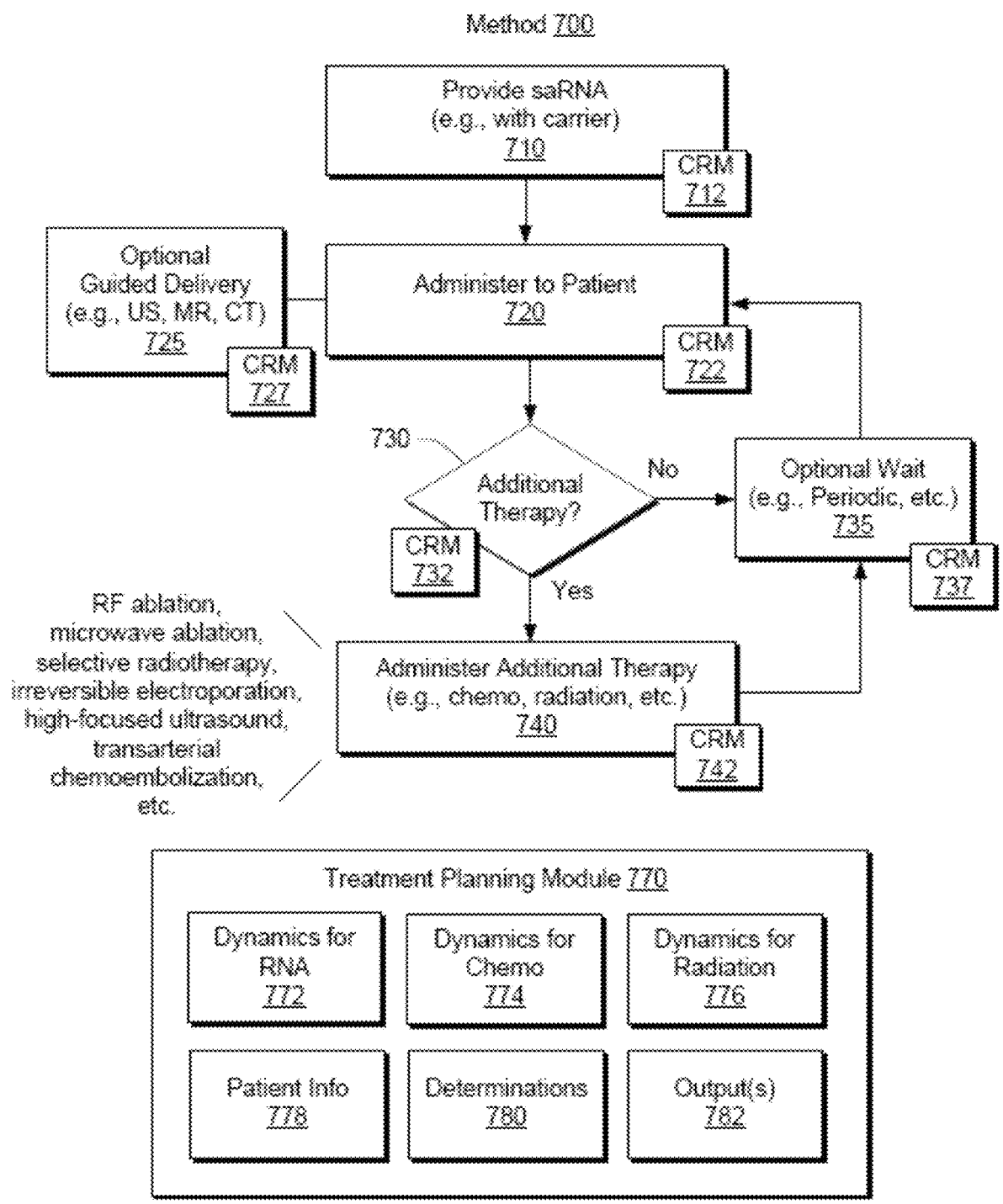
FIG. 7 is a block diagram of an example of a method.

FIG. 7 shows a block diagram of a method 700. In a provision block 710, a saRNA is provided, optionally with a carrier. For example, a designed saRNA may optionally be carried with a liposome or an aptamer or an RNA aptamer to a liver cancer such as a liver cancer that has metastasized outside the liver. In an administration block 720, the saRNA (and optionally carrier) is administered to a patient (e.g., a human subject). As an example, for liver tumours, a designed saRNA may be administered to reach the liver of a patient by systemic injection or local by percutaneous direct injection. Whether for a liver tumour or other type of tumour, administration may be guided by a guidance technique per block 725. Guidance techniques may include ultrasound, fluoroscopy, MR, CT, laparotomo or laparoscopy of endovascular delivery, etc. As described herein, administration may be via oral delivery.

In the example of FIG. 7, an additional therapy may be provided, as indicated by a decision block 730. An additional therapy may optionally be selected from one or more of the following therapies RF ablation, microwave ablation, selective radiotherapy, irreversible electroporation, high-focused ultrasound, transarterial chemoembolization, etc. As indicated, if the decision block 730 decides that one or more additional therapies are to be delivered, then the method 700 enters an additional therapy block 740. If the decision block 730 decides that no additional therapy is to be delivered, the method 700 enters an optional wait block 735 and then continues at the administration block 720, as appropriate. For example, for a therapy that administers saRNA to a patient (e.g., in other than a zero-order fashion), a dose may diminish in effectiveness over a period of days. Thus, the wait block 735 may provide a wait time before administration of a subsequent dose. As an example, where doses are administered, a dose may be given to a patient several times a week (e.g., two to three doses a week for prevention or treatment). As described herein, one or more additional therapies may present factors that determine or alter a wait time between successive doses of saRNA.

Also shown in FIG. 7 are various devices 712, 722, 727, 732, 737 and 742, which may be storage media configured to store instructions for performing one or more actions of the associated blocks. For example, these may be one or more computer-readable media that include information such as processor- or computer-executable instructions. While shown individually, a single storage medium may include instructions for more than one of the blocks. A storage medium may be a hard drive, an optical disk, memory (e.g., a memory card), etc.

FIG. 7 also shows a treatment planning module 770. In the example of FIG. 7, the module 770 includes a dynamics for RNA block 772, a dynamics for chemotherapy block 774, a dynamics for radiation therapy block 776, a patient information block 778, a determinations block 780 and an output block 782. As described herein, RNA, as administered, may have particular dynamics and one or more other therapies may have particular dynamics. As described herein, opportunities exist for synergies between an RNA therapy (e.g., saRNA) and one or more other therapies. The treatment planning module 770 of FIG. 7 may be part of a computing system (e.g., in the form of computer-executable instructions) that allows for automatic or interactive planning of treatment for a patient or patients.

Figure 8:
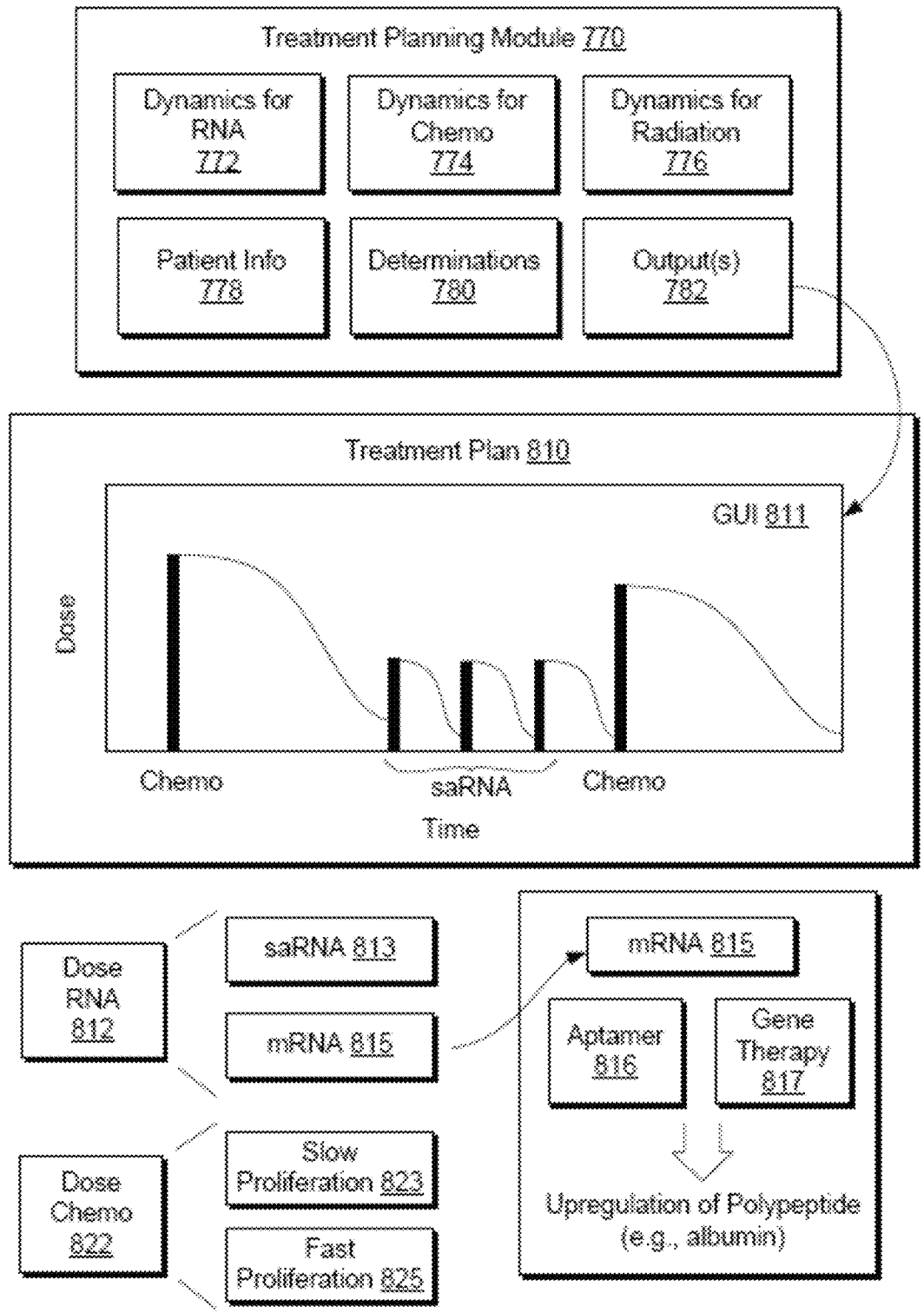
FIG. 8 is a block diagram of an example of a treatment plan and other examples of techniques, technologies, etc.

FIG. 8 shows the treatment planning module 770 of FIG. 7, which may be made of multiple sub-modules, along with an example of a treatment plan 810 displayed (e.g., rendered) graphically as a graphical user interface (GUI) 811. Accordingly, the sub-module 782 may include instructions to forming a GUI that provides for input by a user to interact with the planning module 770. For example, a user may be able to select or adjust dose and types of therapies to optimize a treatment plan for a patient (see, e.g., saRNA doses given between chemo doses). Kinetics of action, clearance, etc., may be taken into account during planning (e.g., as provided by a dynamics sub-module).

FIG. 8 also shows a RNA dose 812, which may be saRNA 813 or mRNA 815. As to the mRNA dose 815, this may be provided with an aptamer 816 or with gene therapy 817, for example, to cause upregulation of a polypeptide (e.g., albumin or other polypeptide). FIG. 8 also shows a chemo dose 822 as an example, which may be chemotherapy suited for slow proliferation cells 823 or chemotherapy suited for fast proliferation cells 825. Factors such as cell cycle time, S-phase duration, etc., have been reported as being germane to effectiveness of chemotherapy. More particularly, cell proliferation kinetics can be a factor as to overall effectiveness of chemotherapy.

As described herein, a dose or doses of RNA (e.g., saRNA) may be administered to a patient (e.g., to tumor cells, etc.) as a mechanism to decrease proliferation after, before or after and before administration of chemotherapy. As chemotherapy may be delivered in spread out doses (e.g, due to toxicity risk to a patient), administration of saRNA in a period between chemo doses may act to optimize overall treatment of a patient.

As described herein, a method can include administering saRNA to cause a cell to upregulate production of a polypeptide (e.g., "naturally secreted") by the cell before it turns cancerous or pre-cancerous. For example, albumin is a polypeptide naturally secreted by various cells (e.g., before such cells turn cancerous or pre-cancerous). As described herein, a method can include administering saRNA to cause an undifferentiated cell to revert to a differentiated cell (e.g., to shift cell behavior of a cell towards behavior more characteristic of a differentiated cell).

Figure 9:
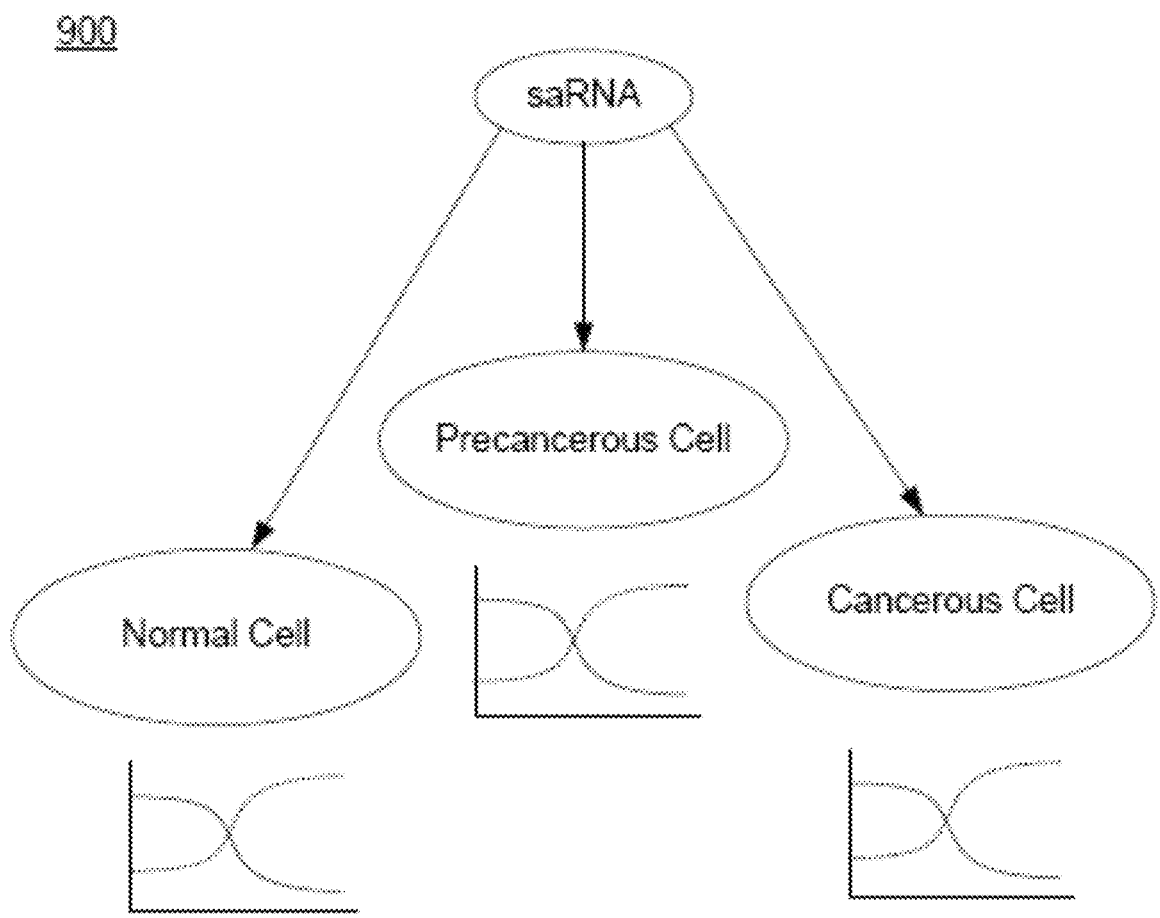
FIG. 9 is a diagram of saRNA being delivered to one or more types of cells.

FIG. 9 shows a diagram of saRNA being delivered to a normal cell, a precancerous cell and a cancerous cell along with illustrative plots of rate of molecule production and rate of cell proliferation. As indicated, saRNA can be delivered to one or more types of cells, cause increase in rate of production of a molecule and cause decrease in rate of cell proliferation.

As described herein, short activating RNA can include a sequence of units to cause upregulation of a polypeptide of a mammalian cell where production of the polypeptide by the mammalian cell impacts negatively proliferation capability of the mammalian cell. As described herein, a polypeptide (as associated with saRNA) may be a naturally secreted polypeptide of a mammalian cell in its natural state. As described herein, a polypeptide (as associated with sa RNA) may be albumin.

As described herein, saRNA may be provided or designed or designed and provided) for a hepatocyte. More generally, saRNA may be provided or designed or designed and provided for a normal cell, a precancerous cell, a cancerous cell where such cells may be mammalian cells.

As described herein, a method can include diagnosing a patient with a condition characterized by excessive proliferation of a type of cell; and designing a short activating RNA to upregulate production of a polypeptide by the type of cell wherein the upregulated production of the polypeptide impacts negatively proliferation capability of the type of cell. Such a method may further include producing the short activating RNA. Such a method may further include administering the designed short activating RNA to the patient. As to diagnosing, a method may include diagnosing liver cancer. As mentioned, a method can include administering an additional therapy (e.g., non-saRNA therapy) that targets a type of cell associated with a saRNA therapy. Such an additional therapy may be chemotherapy, radiation therapy, RF ablation therapy, microwave ablation therapy or other therapy.

As described herein, a method can include designing saRNA by executing one or more instructions stored on a computer-readable storage medium responsive to providing a transcription start site for a gene having a coding region for the polypeptide.

As described herein, one or more computer-readable media can include computer-executable instructions to instruct a computing system to: receive a transcription start site for a gene having a coding region for albumin; select a bounded region about the transcription start site; characterize strings of units as to saRNA candidates for upregulating production of albumin; and output one or more characterized strings of units as preferred candidates for manufacture of saRNA molecules for administration to a human subject to treat liver cancer.

Further embodiments of the invention are set out below:

1. Short activating RNA comprising:
a sequence of units to cause upregulation of a polypeptide of a mammalian cell wherein production of the polypeptide by the mammalian cell impacts negatively proliferation capability of the mammalian cell.

2. The short activating RNA of embodiment 1 wherein the polypeptide comprises a naturally secreted polypeptide of the mammalian cell in its natural state.

3. The short activating RNA of embodiment 1 wherein the polypeptide comprises albumin.

4. The short activating RNA of embodiment 1 wherein the mammalian cell comprises a hepatocyte.

5. The short activating RNA of embodiment 1 wherein the mammalian cell comprises a cancer cell.

6. A method comprising: diagnosing a patient with a condition characterized by excessive proliferation of a type of cell; and designing a short activating RNA to upregulate production of a polypeptide by the type of cell wherein the upregulated production of the polypeptide impacts negatively proliferation capability of the type of cell.

7. The method of embodiment 6 further comprising producing the short activating RNA.

8. The method of claim 6 further comprising administering the designed short activating RNA to the patient.

9. The method of embodiment 6 wherein the diagnosing diagnoses liver cancer.

10. The method of embodiment 6 wherein the designing comprises executing one or more instructions stored on a computer-readable storage medium responsive to providing a transcription start site for a gene having a coding region for the polypeptide.

11. The method of embodiment 6 further comprising administering an additional therapy that targets the type of cell.

12. The method of embodiment 11 wherein the additional therapy comprises a therapy selected from a group consisting of chemotherapy, radiation therapy, RF ablation therapy, and microwave ablation therapy.

13. One or more computer-readable media comprising computer-executable instructions to instruct a computing system to: receive a transcription start site for a gene having a coding region for albumin; select a bounded region about the transcription start site; characterize strings of units as to saRNA candidates for upregulating production of albumin; and output one or more characterized strings of units as preferred candidates for manufacture of saRNA molecules for administration to a human subject to treat liver cancer.

14. A short activating RNA includes a sequence of units to cause up-regulation of a polypeptide of a mammalian cell where production of the polypeptide by the mammalian cell impacts negatively proliferation capability of the mammalian cell.

Various other examples of technologies, techniques, devices, assemblies, systems, methods, etc., are also disclosed.

Although some examples of methods, devices, systems, arrangements, etc., have been illustrated in the accompanying Drawings and described in the foregoing Detailed Description, it will be understood that the example embodiments disclosed are not limiting, but are capable of numerous rearrangements, modifications and substitutions without departing from the spirit set forth and defined by the following claims.

Some References Incorporated by Reference Herein:

Akira, S., Isshiki, H., Sugita, T., Tanabe, O., Kinoshita, S., Nishio, Y., Nakajima, T., Hirano, T., and Kishimoto, T. (1990). A nuclear factor for IL-6 expression (NF-IL6) is a member of a C/EBP family. EMBO J 9, 1897-1906.

Akira, S., Nishio, Y., Inoue, M., Wang, X. J., Wei, S., Matsusaka, T., Yoshida, K., Sudo, T., Naruto, M., and Kishimoto, T. (1994). Molecular cloning of APRF, a novel IFN-stimulated gene factor 3 p91-related transcription factor involved in the gp130-mediated signaling pathway. Cell 77, 63-71.

Barone, M. V., Crozat, A., Tabaee, A., Philipson, L., and Ron, D. (1994). CHOP (GADD153) and its oncogenic variant, TLS-CHOP, have opposing effects on the induction of G1/S arrest. Genes Dev 8, 453-464.

Buck, M., Turler, H., and Chojkier, M. (1994). LAP (NF-IL-6), a tissue-specific transcriptional activator, is an inhibitor of hepatoma cell proliferation. EMBO J 13, 851-860.

Cao, Z., Umek, R. M., and McKnight, S. L. (1991). Regulated expression of three C/EBP isoforms during adipose conversion of 3T3-L1 cells. Genes Dev 5, 1538-1552.

Chang, C. J., Chen, T. T., Lei, H. Y., Chen, D. S., and Lee, S. C. (1990). Molecular cloning of a transcription factor, AGP/EBP, that belongs to members of the C/EBP family. Mol Cell Biol 10, 6642-6653.

Courtois, G., Baumhueter, S., and Crabtree, G. R. (1988). Purified hepatocyte nuclear factor 1 interacts with a family of hepatocyte-specific promoters. Proc Natl Acad Sci USA 85, 7937-7941.

Descombes, P., Chojkier, M., Lichtsteiner, S., Falvey, E., and Schibler, U. (1990). LAP, a novel member of the C/EBP gene family, encodes a liver-enriched transcriptional activator protein. Genes Dev 4, 1541-1551.

Gordon, M. Y., Levicar, N., Pai, M., Bachellier, P., Dimarakis, I., Al-Allaf, F., M'Hamdi, H., Thalji, T., Welsh, J. P., Marley, S. B., et al. (2006). Characterization and clinical application of human CD34+ stem/progenitor cell populations mobilized into the blood by granulocyte colony-stimulating factor. Stem Cells 24, 1822-1830.

Hayhurst, G. P., Lee, Y. H., Lambert, G., Ward, J. M., and Gonzalez, F. J. (2001). Hepatocyte nuclear factor 4alpha (nuclear receptor 2A1) is essential for maintenance of hepatic gene expression and lipid homeostasis. Mol Cell Biol 21, 1393-1403.

Itoh, T., Shiro, T., Seki, T., Nakagawa, T., Wakabayashi, M., Inoue, K., and Okamura, A. (2000). Relationship between p53 overexpression and the proliferative activity in hepatocellular carcinoma. Int J Mol Med 6, 137-142.

Johnson, P. F. (2005). Molecular stop signs: regulation of cell-cycle arrest by C/EBP transcription factors. J Cell Sci 118, 2545-2555.

Kubicka, S., Kuhnel, F., Zender, L., Rudolph, K. L., Plumpe, J., Manns, M., and Trautwein, C. (1999). p53 represses CAAT enhancer-binding protein (C/EBP)-dependent transcription of the albumin gene. A molecular mechanism involved in viral liver infection with implications for hepatocarcinogenesis. J Biol Chem 274, 32137-32144.

Landschulz, W. H., Johnson, P. F., and McKnight, S. L. (1988). The leucine zipper: a hypothetical structure common to a new class of DNA binding proteins. Science 240, 1759-1764.

Lee, Y. H., Sauer, B., Johnson, P. F., and Gonzalez, F. J. (1997). Disruption of the c/ebp alpha gene in adult mouse liver. Mol Cell Biol 17, 6014-6022.

Lichtsteiner, S., and Schibler, U. (1989). A glycosylated liver-specific transcription factor stimulates transcription of the albumin gene. Cell 57, 1179-1187.

Maeda, Y., Seidel, S. D., Wei, G., Liu, X., and Sladek, F. M. (2002). Repression of hepatocyte nuclear factor 4alpha tumor suppressor p53: involvement of the ligand-binding domain and histone deacetylase activity. Mol Endocrinol 16, 402-410.

Maire, P., Wuarin, J., and Schibler, U. (1989). The role of cis-acting promoter elements in tissue-specific albumin gene expression. Science 244, 343-346.

Mueller, C. R., Maire, P., and Schibler, U. (1990). DBP, a liver-enriched transcriptional activator, is expressed late in ontogeny and its tissue specificity is determined post-transcriptionally. Cell 61, 279-291.

Nagao, T., Kondo, F., Sato, T., Nagato, Y., and Kondo, Y. (1995). Immunohistochemical detection of aberrant p53 expression in hepatocellular carcinoma: correlation with cell proliferative activity indices, including mitotic index and MIB-1 immunostaining. *Hum Pathol* 26, 326-333.

Ng, I. O., Lai, E. C., Chan, A. S., and So, M. K. (1995). Overexpression of p53 in hepatocellular carcinomas: a clinicopathological and prognostic correlation. J Gastroenterol Hepatol 10, 250-255.

Panduro, A., Shalaby, F., and Shafritz, D. A. (1987). Changing patterns of transcriptional and post-transcriptional control of liver-specific gene expression during rat development. Genes Dev 1, 1172-1182.

Pietrangelo, A., Panduro, A., Chowdhury, J. R., and Shafritz, D. A. (1992). Albumin gene expression is down-regulated by albumin or macromolecule infusion in the rat. J Clin Invest 89, 1755-1760.

Pietrangelo, A., and Shafritz, D. A. (1994). Homeostatic regulation of hepatocyte nuclear transcription factor 1 expression in cultured hepatoma cells. Proc Natl Acad Sci USA 91, 182-186.

Poli, V., Mancini, F. P., and Cortese, R. (1990). IL-6DBP, a nuclear protein involved in interleukin-6 signal transduction, defines a new family of leucine zipper proteins related to C/EBP. Cell 63, 643-653.

Prives, C. (1998). Signaling to p53: breaking the MDM2-p53 circuit. Cell 95, 5-8.

Tilghman, S. M., and Belayew, A. (1982). Transcriptional control of the murine albumin/alpha-fetoprotein locus during development. Proc Natl Acad Sci USA 79, 5254-5257.

Trautwein, C., Boker, K., and Manns, M. P. (1994). Hepatocyte and immune system: acute phase reaction as a contribution to early defence mechanisms. Gut 35, 1163-1166.

Wang, N. D., Finegold, M. J., Bradley, A., Ou, C. N., Abdelsayed, S. V., Wilde, M. D., Taylor, L. R., Wilson, D. R., and Darlington, G. J. (1995). Impaired energy homeostasis in C/EBP alpha knockout mice. Science 269, 1108-1112.

Williams, S. C., Cantwell, C. A., and Johnson, P. F. (1991). A family of C/EBP-related proteins capable of forming covalently linked leucine zipper dimers in vitro. Genes Dev 5, 1553-1567.

Zhong, Z., Wen, Z., and Darnell, J. E., Jr. (1994). Stat3: a STAT family member activated by tyrosine phosphorylation in response to epidermal growth factor and interleukin-6. Science 264, 95-98.

Tables

TABLE 1

|  | ID | Target (Sense) | SEQ ID NO | Anti-sense (Guide) | SEQ ID NO |
|---|---|---|---|---|---|
| human albumin | PR1 | CCUUGUAAGACUUCACAAA | 5 | UUUGUGAAGUCUUACAAGG | 6 |
|  | PR2 | UGGAUAGGUCUUUGGGAUA | 7 | UAUCCCAAAGACCUAUCCA | 8 |
|  | PR3 | AAGAGUUAAGCUUUAAAUU | 9 | AAUUUGGGACUUAACUCUU | 10 |
|  | PR4 | GACUAAAUCCCUUGUGUAU | 11 | AUACACAAGGGAUUUAGUC | 12 |
| human rCEBPra | AW1 | CGGUCAUUGUCACUGGUCA | 13 | UGACCAGUGACAAUGACCG | 14 |
|  | AW2 | AGCUGAAAGGAUUCAUCCU | 15 | AGGAUGAAUCCUUCCAGCU | 16 |
|  | NR1 | ACAUAGUCCCAGUGAUUAA | 17 | UUAAUCACUGGGACUAUGU | 18 |
|  | NR2 | GAAUAAGACUUUGUCCAAU | 19 | AUUGGACAAAGUCUUAUUC | 20 |
| human rCEBPra | PR1 | GCGCGGAUUCUCUUUCAAA | 21 | UUUGAAAGAGAAUCCGCGC | 22 |
|  | PR2 | CCAGGAACUCGUCGUUGAA | 23 | UUCAACGACGAGUUCCUGG | 24 |
| human HNF4A | PR1 | GAGCUUUGGGCCCGUAAGA | 25 | UCUUACGGGCCCAAAGCUC | 26 |
|  | PR2 | GGUGGAUACGUUAAAGAGU | 27 | ACUCUUUAACGUAUCCACC | 28 |
|  | PR3 | CCCAGAAUGCCUGUGAUCA | 29 | UGAUCACAGGCAUUCUGGG | 30 |
|  | PR4 | CCGAUGUUCAGUUAUCAAU | 31 | AUUGAUAACUGAACAUCGG | 32 |
|  | BC1 | GAAGAUUGCUCGUGCAAAU | 33 | AUUUGCACGAGCAAUCUUC | 34 |
|  | BC2 | CAGAUAUGCUCCAGUGAUG | 35 | CAUCACUGGAGCAUAUCUG | 36 |

TABLE 2

|  | ID | Target (Sense) | SEQ ID NO | Anti-sense (Guide) | SEQ ID NO |
|---|---|---|---|---|---|
| Mouse albumin | PR1 | GAAAGACUCGCUCUAAUAU | 37 | AUAUUAGAGCGAGUCUUUC | 38 |
|  | PR2 | CUAUGAGACCGUAAUAAAU | 39 | AUUUAUUACGGUCUCAUAG | 40 |
|  | PR3 | CCAUUAUUGUCAUCAAAGA | 41 | UCUUUGAUGACAAUAAUGG | 42 |
|  | PR4 | AAGUUAGAAUCUUCCAUAA | 43 | UUAUGGAAGAUUCUAACUU | 44 |

EXAMPLES

Example 1—Designing Short RNAs for Upregulating Albumin Expression

The gene sequences of genes involved in albumin production were selected for designing short activating RNA molecules for its specific activation. Particularly suitable are the albumin gene, the CEBPA gene and/or the HNF4α gene.

Four parameters were used: 1) targeting gene annotations from UCSC RefSeq database; 2) targeted sequence from antisense RNA; 3) promoter selection of antisense sequences; and 4) identification of candidate short activating RNAs.

First, the method downloads information about the target's genomic location, orientation, and transcriptional structure from available databases (RefSeq at UCSC). Second, given a database of RNA transcripts with known read direction, such as the UCSC Spliced EST track, our method searches the database for transcripts that are antisense to and in the vicinity of the target gene. More specifically, the method identifies antisense transcripts that (a) overlap the target's promoter and the target mRNA's 5' end; (b) overlap the target mRNA; (c) are at most 20-100 kb upstream of the target's transcription start site (TSS); or (d) are at most 20-100 kb downstream of the target's poly-adenylation site. The method uses these four criteria as hierarchical filters such that if it finds antisense transcripts that for example satisfy criterion (a), the method does not consider the three other criteria. Third, based on the target's TSS, the method downloads the antisense genomic sequence from a fixed size region upstream and downstream of the TSS. The typical region size used by the method is 500 nts upstream and downstream of TSS, but larger or smaller sizes can also be used. Fourth, the method designs siRNAs that give effective and specific down-regulation of the antisense target sequence. The method (a) uses a siRNA design algorithm, such as GPboost (Seatrom P, 2004), to identify candidate effective siRNAs; (b) removes all candidate siRNAs with aaaa, cccc, gggg, or uuuu motifs and GC content less than 20% or greater than 55%; (c) removes all candidates that have Hamming distance less than two to all potential off-target transcripts; and (d) returns a given number of remaining non-overlapping siRNAs sorted by their predicted siRNA knockdown efficacy. The method returns the two highest scoring saRNAs for a given antisense target sequence.

Following a denaturation step at 90° C., paired saRNA oligonucleotides were annealed using 50 mM Tris-HCl, pH 8.0, 100 mM NaCl and 5 mM EDTA.

Example 2—Upregulation of Albumin Expression Through Transfection with Albumin saRNA Materials and Methods 25 nM of annealed Albumin saRNA designed as described in Example 1 was transfected onto a monolayer of cell using Nanofectamine (PAA, UK) following the manufacturer's instructions. This process was repeated three times. The sequences of the saRNA that were used for this study were human albumin PR1 (SEQ ID NO:5 and SEQ ID NO:6), human albumin PR2 (SEQ ID NO:7 and SEQ ID NO:8), human albumin PR3 (SEQ ID NO:9 and SEQ ID NO:10) and human albumin PR4 (SEQ ID NO:11 and SEQ ID NO:12), as shown in Table 1. A random, scrambled RNA molecule was used as control.

After transfection, the isolation of total RNA was performed using the RNAqueous-Micro kit (Ambion, UK) following the manufacturer's instructions. Briefly, the cells were gently centrifuged followed by 3 pulses of sonication at Output 3 in Lysis buffer (Ambion, UK). The cell lysates were then processed through an RNA binding column, followed by multiple washes and elution. The total RNA isolated was quantified by a Nanodrop 2000 spectrophotometer. 500 ng of total extracted RNA was processed for elimination of genomic DNA followed by reverse transcription using the QuantiTect® Reverse Transcription kit from Qiagen.

The isolated RNA extracts were analysed using quantitative reverse transcriptase (qRT-PCR). Briefly, the extracts were reverse transcribed using First strand cDNA synthesis kit (Qiagen). The cDNA was then amplified for quantitative analysis using QuantiFast® SYBR® Green PCR Kit from Qiagen. Amplification was performed using Applied Biosystems 7900HT FAST-Real-Time System with 40 cycle conditions at 95° C. for 15 seconds and 60° C. for 45 seconds with a total volume of 25 µl per sample. Amplified products were then analysed using Applied Biosystems RQ Manager 1.2.1. 5 independent experiments were amplified in triplicates for quantitative analysis. Student T-Test scoring was performed at 99% confidence intervals.

Albumin production was determined within the cells through the use of an albumin ELISA. Briefly, the cells were grown in phenol-red free RPMI media in the presence of charcoal stripped FCS. Following three sets of saRNA transfections at 8 hrs, 16 hrs and 24 hrs, the culture media was collected for total Albumin ELISA (Assay Max, Albumin ELISA, Assay Pro USA) following the manufacturer's instructions.

Results

The effects of the transfection with the albumin saRNA oligonucleotides on albumin production are illustrated in FIG. 2. An RT-PCR profile of the mRNA levels showed an increase in albumin levels only in cells transfected with saRNAs.

Figure 10A:
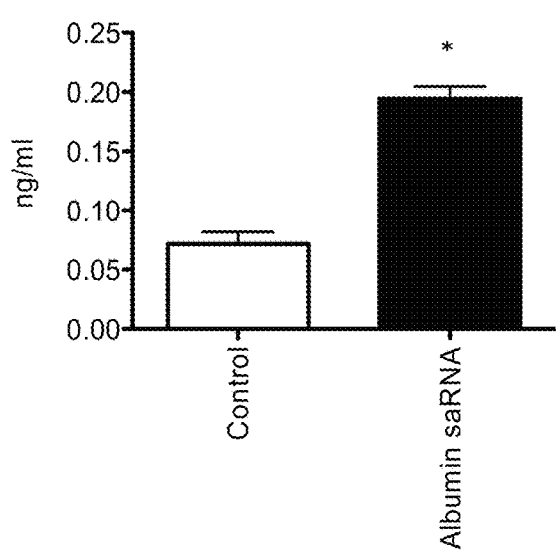
FIG. 10A-10C shows the in vitro effects of transfecting liver cells with albumin saRNA (see Example 2). Data represent mean, SEM from three independent transfections.
Figure 10B:
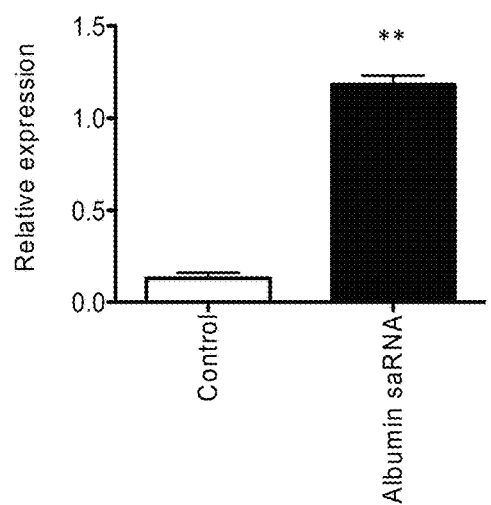
Figure 10C:
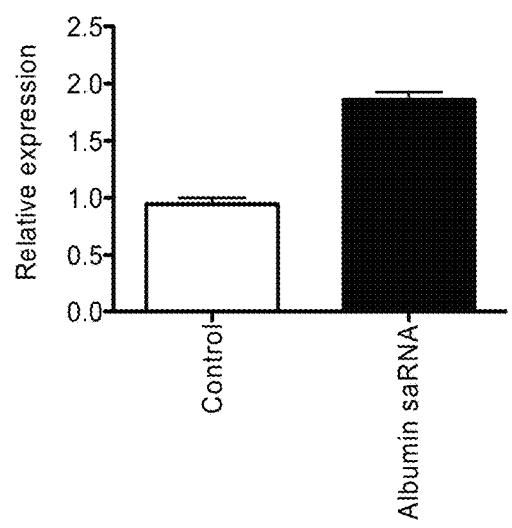

FIG. 10A-10C show that a significant increase in the albumin mRNA is detected in the transfected HepG2 cell line (FIG. 10B) and rat liver epithelial cells (FIG. 10C) as compared to control, and this in turn leads to a significant increase in albumin production in the transfected cell lines (FIG. 10A), data only shown for HepG2).

Example 3—Inhibition of the Proliferation of Cells Through Transfection with Albumin saRNA HepG2 cells and rat liver epithelial cells were transfected with albumin saRNAs as described in Example 2, i.e. the same saRNAs were used in this Example as in Example 2. Cell proliferation within the rat liver epithelial cells and HepG2 cells respectively was measured using the WST-1 proliferation assay. Briefly, the cell proliferation reagent tetrazolium salt, 4-[3-(4-iodophenyl)2-(4nitrophenyl)2H-5-tetrazolio]1,3benzene disulfonate (Roche Applied Science, UK) was added (e.g., following the manufacturer's instructions). The colorimetric assay was then incubated for 30 minutes to allow cleavage of the tetrazolium salt WST-1 to a formazan dye by mitochondrial succinate-tetrazolium reductase in viable cells. The quantity of formazan dye, which is directly related to the number of metabolically active cells proliferating was measured at Amax450 nm in a multiwall plate reader.

Cell proliferation and viability was significantly inhibited by each of the saRNAs. Results obtained with the HepG2 cell line are shown in FIG. 3.

Example 4—Upregulation of Albumin and Inhibition of Cell Proliferation Through the Transfection with CEBPA saRNA In Vitro The following saRNA duplexes (sense/antisense) targeted for CEBPA was used for this study:

```
AW1 Sense strand:
                                    (SEQ ID NO: 13)
CGGUCAUUGUCACUGGUCA AW1 anti-sense strand:
                                    (SEQ ID NO: 14)
UGACCAGUGACAAUGACCG AW2 Sense strand:
                                    (SEQ ID NO: 15)
AGCUGAAAGGAUUCAUCCU AW2 anti-sense strand:
                                    (SEQ ID NO: 16)
AGGAUGAAUCCUUUCAGCU
```

Synthetic saRNA duplexes (above) targeting the 3'UTR promoter region of the CEBPA was transfected into either cell lines or primary CD34+ cells (Omnicytes) using the liposomal method (Nanofectin). Changes in the transcript levels of CEBPA and albumin was measured quantitatively by qPCR. Additionally changes in cellular proliferation was measured using tetrazolium salt, 4-[3-(4-iodophenyl)2-(4nitrophenyl)2H-5-tetrazolio]1,3benzene disulfonate (WST-1) assay.

Figure 11A:
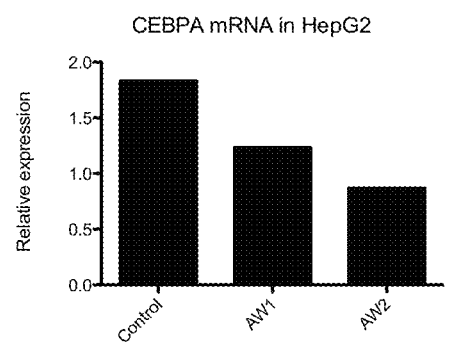
FIG. 11A-11D show the effects of transfecting the HepG2 cell line with CEBPA saRNA constructs AW1 and AW2 against control (see Example 4).
Figure 11B:
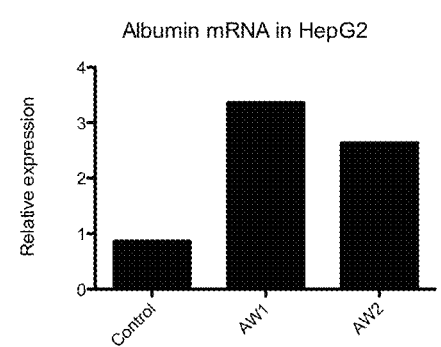
Figure 11C:
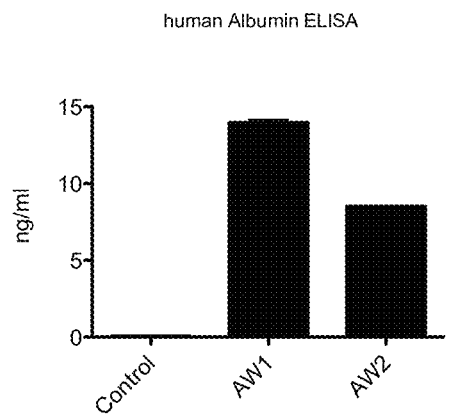
Figure 11D:
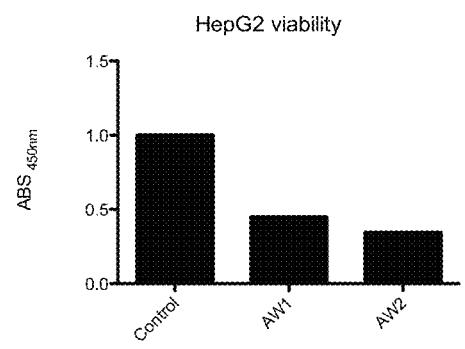

Since the expression of CEBPA in HepG2 cells is lower when compared to other cultured human hepatocytes, HepG2 cells were used to investigate the effects of transfecting AW1 and AW2. Following three doses of transfection over a culture period of 48 hours, HepG2 cells were harvested and analysed for mRNA analysis. No significant changes in the mRNA levels of CEBPA was observed during this culture period (FIG. 11A). This is unsurprising as CEBPA shows early and fast decay during initial stages of culture. In contrast, an increase in mRNA transcript levels of albumin was observed (FIG. 11B). To confirm if albumin increase in mRNA also reflected its translation to protein, a functional enzyme-linked immunosorbent assay (ELISA) was performed. saRNA transfected cells were cultured in a serum free/charcoal stripped media to remove any source of exogenous albumin. Following the 48 hour culture period in the presence of either AW1 or AW2 the cell culture medium was isolated and processed for detection of human albumin using a commercially available kit. A significant increase of albumin expression was detected in cells transfected in saRNA when compared to untransfected cells (FIG. 11C). We also performed a WST-1 proliferation assay in the transfected HepG2 cells. A reduction in cell proliferation was observed (FIG. 11D).

Figure 12A:
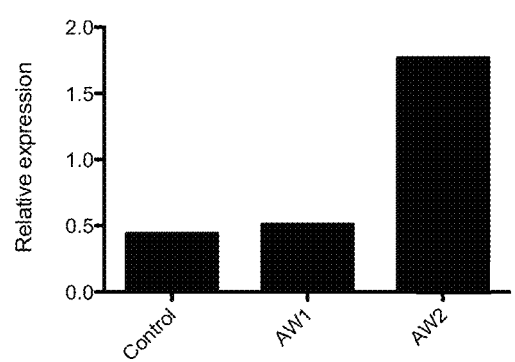
FIG. 12A-12C show the effects of transfecting the DU145 prostate cancer epithelial cell line with CEBPA saRNA constructs AW1 and AW2 against control (see Example 4).
Figure 12B:
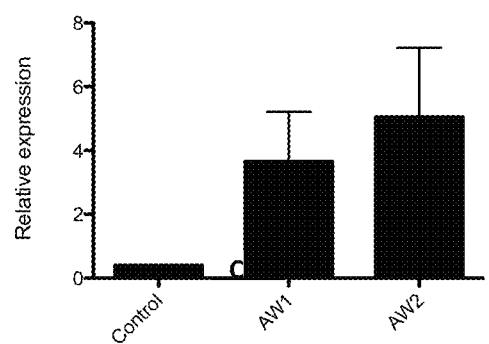
Figure 12C:
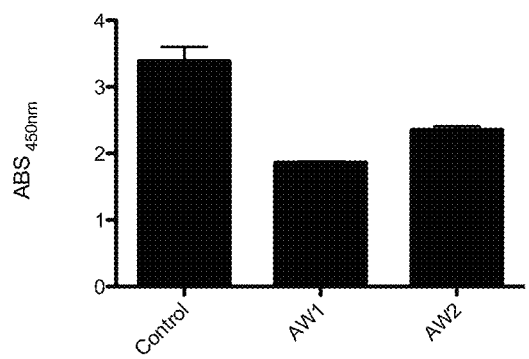

We next determined if AW1 or AW2 would successfully induce a positive regulation of albumin transcript or translation in non-hepatic cells, namely a prostate cancer epithelial cell line (DU145) (FIG. 12A-12C) and a healthy adult haematopoietic CD34 cell line. These cell lines were transfected with AW1 and AW2 as described above, following three doses over a period of 48 hours. The cells were then harvested and analysed for transcript levels of CEBPA and albumin. The prostate cancer cell line showed a strong increase in CEBPA transcript level when transfected with AW2 relative to AW1 (FIG. 12A) and both transfections induced a significant increase in albumin transcript levels (FIG. 12B). A WST1 assay was also performed. Growth of DU145 was significantly reduced following transfection with CEBPA (FIG. 12C).

AW1 and AW2 also upregulated albumin production in the CD34+ stem cells, but the proliferation of the CD34 cells was not affected by the AW1 and AW2 saRNA constructs (data not shown).

The inventor has successfully established that transfection with saRNA AW1 and AW2 specific to CEBPA has the ability of up-regulating albumin transcript level and protein expression in a human hepatocellular carcinoma line and a prostate cancer epithelial cell line. Furthermore, this increase in albumin protein expression leads to a decrease in cell proliferation. By contrast, the transfection of healthy CD34 cells with saRNA AW1 and AW2 specific to CEBPA did not affect cell proliferation, suggesting that the effect on cell proliferation is specific to cancer cells.

Example 5—Upregulation of Albumin Through the Transfection with Albumin saRNA in Mouse Liver In Vivo Ten Male C57Bl6/J, 8 week old mice were used for the experiment (control group N=5). Approval was obtained from Institutional and Regional Regulatory bodies and all procedures were in compliance with standing National Regulations.

Albumin saRNA oligonucleotides were developed as described in Example 1. Mouse albumin PR2 (SEQ ID NO:39 and SEQ ID NO:40), as shown in Table 2, was chosen for this study. The oligonucleotides were reconstituted with 100 µL of RNase/Dnase free $H_2O$; 50 µL of complex A and 50 µL of complex B (InvivoFectamine, Invitrogen, CA, USA) were mixed, incubated at 50° C. for 30 minutes and were used for tail vein injections. Control animals were injected with equal volume of PBS while a positive control animal received siRNA against Factor 7; a total of 5 control and 5 experimental animals were injected.

After administration, the total RNA was isolated. Frozen tissue sections were placed into scintillation vials containing Trizol and homogenised for 30 seconds. The homogenate was then transferred in Falcon tubes for a further 2 minutes of homogenisation. Chloroform was then added to this and mixed by vortexing followed by a centrifugation step at 12,000 rpm for 15 minutes at 4° C. The aqueous upper phase was then transferred into a fresh microfuge tube where RNA was precipitated using 5 mg/ml of linear acrylamide (Ambion) and isopropanol overnight at −20° C. The RNA was pelleted by centrifugation at 12,000 rpm for 15 minutes at 4° C. and washed with ice cold 70% ethanol. The RNA was pelleted again at 7,500 rpm for 5 minutes at 4° C. The supernatant was removed immediately and the RNA pellet allowed to air dry. The RNA was dissolved in nuclease free water for immediate analysis for RNA integrity using a Bionanalyser.

The isolated RNA was analysed using qRT-PCR as described in Example 2. Albumin production was determined using an Albumin ELISA as described in Example 2.

Figure 13A:
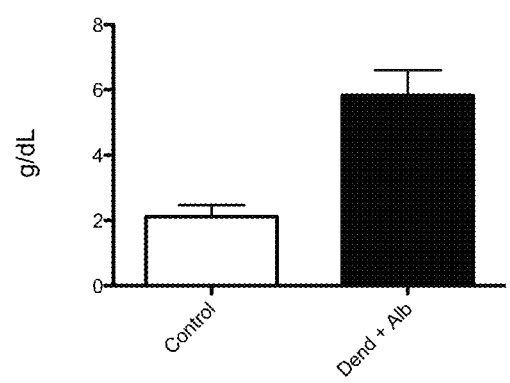
FIG. 13A-13D show blood analysis of tail injected mice (n=5) for each control, or dendrimer+albumin saRNA group (see Example 5) FIG. 13A Albumin, FIG. 13B gamma glutamyl transpeptidase, FIG. 13C alanine aminotransferase and FIG. 13D aspartate aminotransferase.

FIG. 13A shows that the administration of albumin saRNA oligonucleotides using a dendrimer delivery vehicle to a mouse leads to a significant increase in albumin within the blood circulation.

Figure 13B:
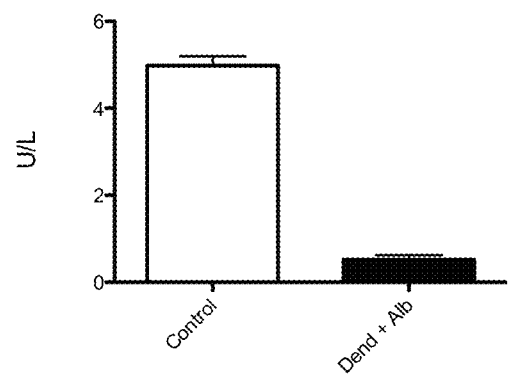
Figure 13C:
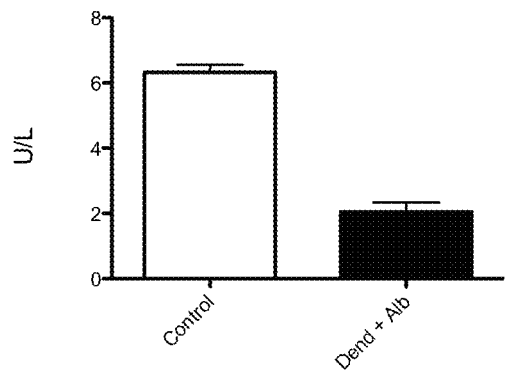
Figure 13D:
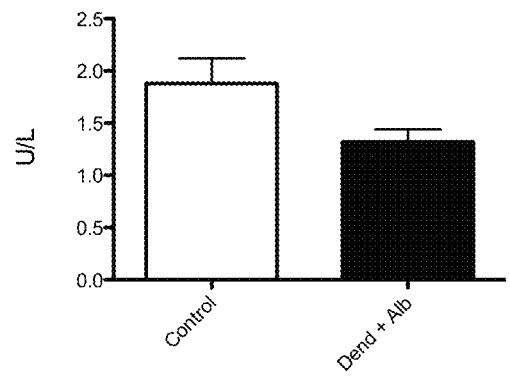
Figure 16A:
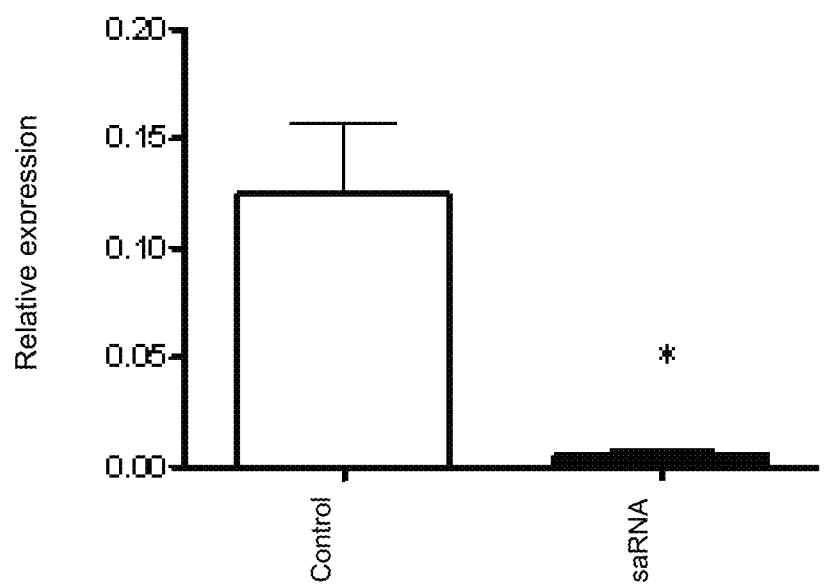
FIG. 16A and FIG. 16B show quantitative analysis of transcript level from tissue biopsies in mice administered with albumin saRNA+dendrimer against control.
Figure 16B:
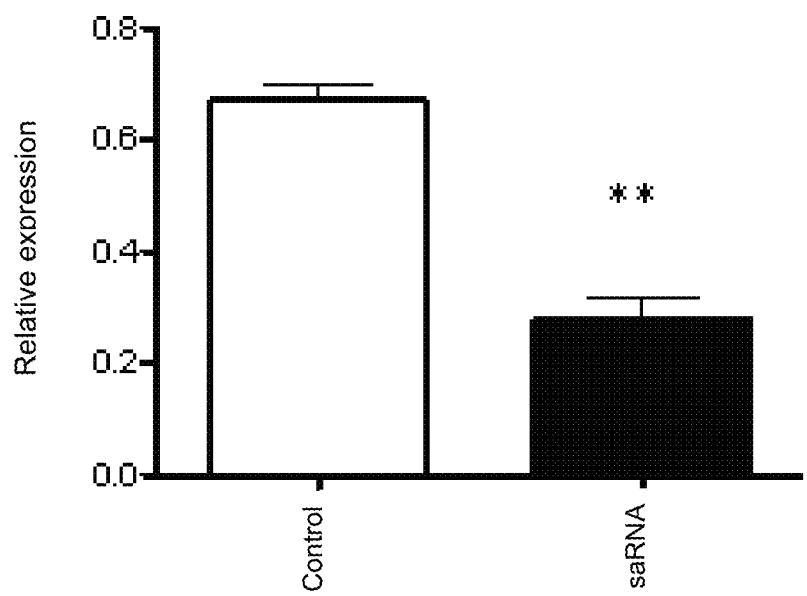

The administration of the albumin saRNA had no dentrimental effects on overall liver function according to the liver function markers gamma glutamyl transpeptidase (FIG. 13B), alanine aminotransferase (FIG. 13C) and aspartate aminotransferase (FIG. 13D) or bilirubin (data not shown). Furthermore, the albumin saRNA was able to downregulate the mRNA expression of the genes which encode a fetoprotein (FIG. 16A) and hepatocyte growth factor (FIG. 16B). As both of these proteins are linked to hepatocyte proliferation, the downregulation of these genes by the saRNA suggests that they are capable of inhibiting proliferation in vivo.

The immunohistochemistry of the mice livers showed that the architecture of the liver acini was preserved, there was no significant portal inflammation or fibrosis, the bile ducts, central venules and the sinusoids were unremarkable, there were not foci of oval cell proliferation, there were no distinct foci of hepatitic necroinflammatory activity, there was not activation of Kuppfer cells, at least not one detectable by morphology, there were no vascular or endothelial alterations, there were not signs of reversible cell injury, i.e. ballooning or steatosis and there were no findings suggestive of increased hepatocellular proliferation, i.e. mitoses, thickened plates, nuclear crowding. In summary, the morphology of the liver remained mostly unchanged by the administration of the albumin saRNA oligonucleotides.

Example 6—Upregulation of Serum Albumin Through the Transfection with CEBPA saRNA in Rats with Cirrhotic Livers The ability of the CEBPA saRNA constructs to increase albumin was assessed on diseased animals, namely rats with cirrhotic livers.

In order to assess the in vivo effects of AW1 (SEQ ID NO: 13 and SEQ ID NO:14) and AW2 (SEQ ID NO:15 and SEQ ID NO:16) on albumin production, rats with cirrhotic livers were administered with AW1 and AW2 constructs and albumin ELISA was used as described in Example 2.

Figure 14:
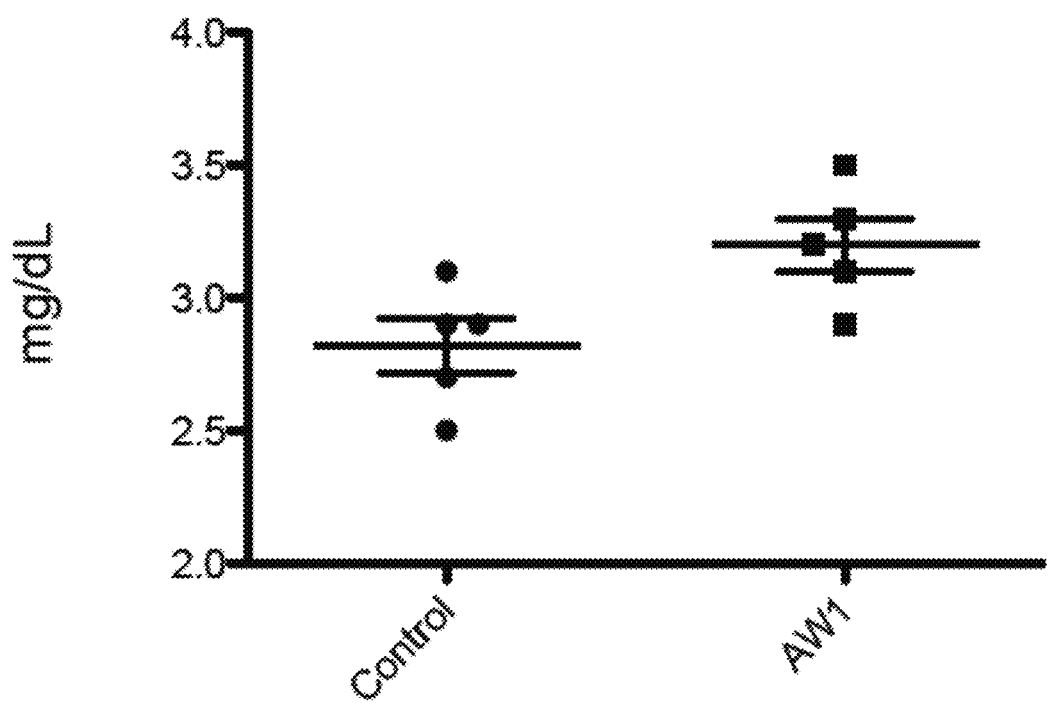
FIG. 14 shows the serum albumin levels after the administration of AW1 saRNA to rats, compared against control. See Example 6. AW1 targets CEBPA (see Table 1 for sequences).
Figure 15:
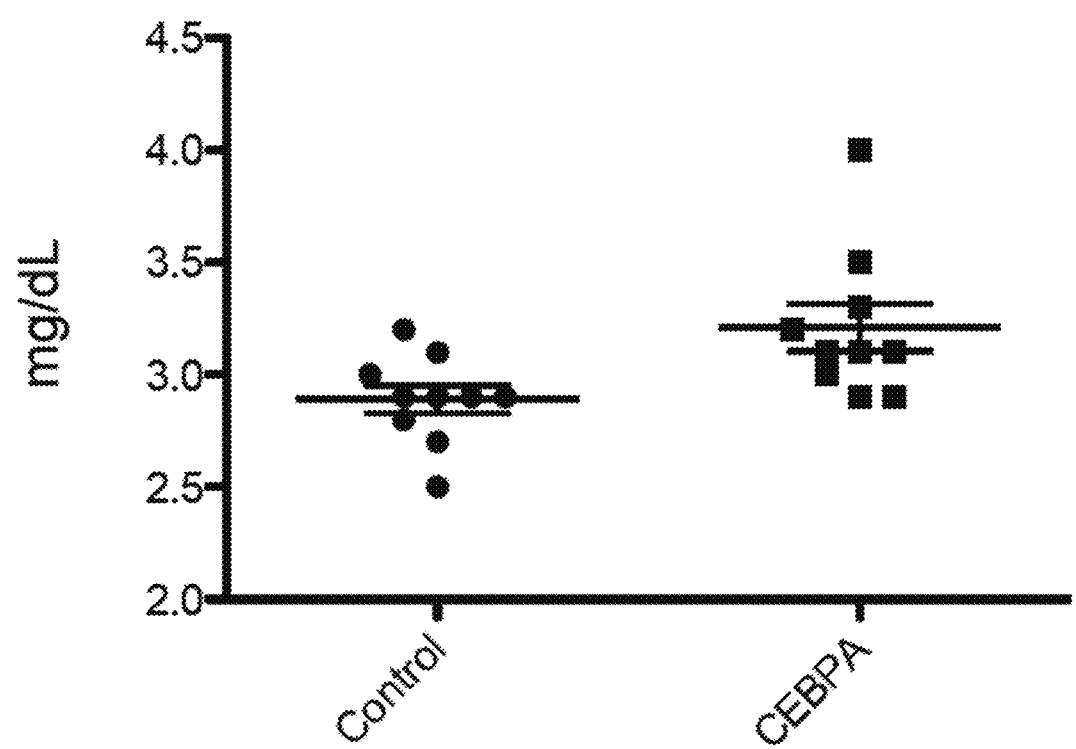
FIG. 15 shows the pooled data regarding serum albumin levels, combining data of AW1 and AW2 (see Table 1 for sequences) administration to rats and comparing against control administration to rats. See Example 6.

The administration of the AW1 construct led to a significant increase in serum albumin (p=0.0288) (FIG. 14). Pooling the AW1 and the AW2 data together shows that the increase in albumin production is even more significant (p=0.0172) (FIG. 15), wherein AW1 and AW2 pooled are labelled "CEBPA"). This shows that effects of the CEBPA saRNA constructs on albumin production can be seen in diseased animals in vivo.

Example 7—Inhibition of Tumor Development and Growth Through Transfection with CEBPA saRNAs in a Rat Tumor Model 20 rats were treated with carbon tetra chloride (CCl4) to induce liver cirrhosis. The rats were treated with 0.2 mL/100 g body weight of CCl4 at concentration of 40 mL/L twice a week for 4 weeks.

Then they were randomised into two groups. A control group was injected with saline in the tail vein. The experimental group injected with three injections of saRNA which upregulates albumin by upregulating CEBPA: AW1 (SEQ ID NO: 13 and SEQ ID NO:14) or AW2 (SEQ ID NO:15 and SEQ ID NO:16) at day 1, 3 and 5. All animals were sacrificed two weeks after the saRNA injection.

The rats treated with saRNA rats had a significantly smaller number of tumours, and the tumours were smaller compared to control (saline-treated) rats. Moreover, the onset of tumour developments was later in the saRNA treated group. AW1 was particularly effective at inhibiting tumour development and growth.

Example 8 Inhibition of Tumor Development and Growth Through Transfection with Albumin-Upregulating saRNAs in an Animal Tumor Model The experiment described in Example 6 or 7 is repeated with mice which have been chemically induced to have liver cancer. Liver cancer is induced using DEN, a genotoxic carcinogen. DEN is typically administered to mice between 12 and 15 days of age by a single intraperitoneal injection (5 μg/g body weight). Using this protocol, 100% of B6C3F1 male mice develop HCCs, on average, 44 wk after intraperitoneal injection of DEN. saRNAs shown in Table 1 are then administered and albumin expression is assayed as described in Example 6.

Tumor diameters are measured with digital calipers, and the tumor volume in $mm^3$ is calculated by the formula: Volume=(width)$^2$×length/2. Tumor development and growth is analysed by determining tumor volume of treated mice compared to control mice.

Example 9—Inhibition of Cancer Cell Proliferation Through the Transfection with Albumin-Upregulating saRNAs in Mice with a Human Tumour Xenograft Human liver tumour cells are cultured in vitro, washed, and injected (3.0×10$^6$ cells) subcutaneously into the lower flank of nude mice (4-6 weeks old). Therapy using saRNAs shown in Table 1 is started after 1-3 weeks when the tumours have reached an average volume of ~50-60 $mm^3$. Tumour diameters are measured with digital calipers, and the tumour volume in $mm^3$ is calculated by the formula: Volume=(width)$^2$×length/2.

saRNA administration and albumin expression assays are carried out as described in Example 6. Tumour development and growth is analysed by determining tumour volume of treated mice compared to control mice.

The invention claimed is:

1. A synthetic short activating RNA (saRNA) which up-regulates the expression of a target gene, wherein the target gene is HNF4a,
wherein the saRNA comprises an antisense strand that has at least 95% sequence identity to a sequence located on the coding strand of the target gene between 500 nucleotides upstream and 500 nucleotides downstream of the transcription start site of the target gene, and wherein said strand has 13-30 nucleotides in length.

2. The saRNA of claim 1, wherein each strand of the saRNA comprises a number of unpaired nucleotides at the 3' end forming 3' overhangs.

3. The saRNA of claim 2, wherein said 3' overhang is UU or UUU.

4. A method of up-regulating the expression of a target gene in a cell, wherein the target gene is HNF4a, comprising transfecting said cell with the saRNA of claim 1.

5. The method of claim 4, wherein the cell is a cancer cell.

6. The method of claim 4, wherein the cell is a liver cell.

7. The method of claim 4, wherein the cell is a liver cancer cell.

8. A synthetic short activating RNA (saRNA) which up-regulates the expression of a target gene, wherein the target gene is HNF4a, and wherein the saRNA is double stranded and comprises an anti-sense strand having a sequence selected from SEQ ID NOs: 26, 28, 30, 32, 34 and 36.

9. The saRNA of claim 8, wherein the saRNA comprises a sense strand having a sequence selected from SEQ ID NOs: 25, 27, 29, 31, 33 and 35.

10. The saRNA of claim 8, wherein the saRNA is double stranded and comprises an anti-sense strand having SEQ ID NO: 30 and a sense strand having SEQ ID NO: 29.

11. The saRNA of claim 10, wherein each strand of the saRNA comprises a number of unpaired nucleotides at the 3' end forming 3' overhangs.

12. The saRNA of claim 11, wherein said 3' overhang is UU or UUU.

13. A method of up-regulating the expression of a target gene in a cell, wherein the target gene is HNF4a, comprising transfecting said cell with the saRNA of claim 8.

* * * * *